US007091397B2

(12) United States Patent
Wassenegger et al.

(10) Patent No.: US 7,091,397 B2
(45) Date of Patent: *Aug. 15, 2006

(54) NUCLEIC ACID MOLECULES ENCODING POLYPEPTIDES HAVING THE ENZYMATIC ACTIVITY OF AN RNA-DIRECTED RNA POLYMERASE (RDRP)

(75) Inventors: Michael Wassenegger, Munich (DE); Leonhard Riedel, Munich (DE); Winfried Schiebel, Gauting (DE); Heinz L Sanger, Berg (DE)

(73) Assignee: Plant Bioscience Limited, Norfolk (GB)

( * ) Notice: Subject to any disclaimer, the term of this patent is extended or adjusted under 35 U.S.C. 154(b) by 668 days.

This patent is subject to a terminal disclaimer.

(21) Appl. No.: 09/782,874

(22) Filed: Feb. 8, 2001

(65) Prior Publication Data

US 2001/0023067 A1    Sep. 20, 2001

Related U.S. Application Data

(62) Division of application No. 08/811,583, filed on Mar. 5, 1997, now Pat. No. 6,218,142.

(51) Int. Cl.
*C12N 15/82* (2006.01)
*C12N 5/04* (2006.01)
*A01H 5/00* (2006.01)
*A01H 5/08* (2006.01)
*A01H 5/10* (2006.01)

(52) U.S. Cl. .................. 800/278; 800/286; 435/419; 536/23.2; 536/23.6

(58) Field of Classification Search ................ 435/69.1, 435/419; 536/23.1; 800/298, 278, 285, 800/286
See application file for complete search history.

(56) References Cited

U.S. PATENT DOCUMENTS 5,495,071 A * 2/1996 Fischhoff et al.
5,498,533 A * 3/1996 Poovaiah et al.

FOREIGN PATENT DOCUMENTS

WO    WO 90/12084    * 10/1990

OTHER PUBLICATIONS

Doerks (TIG 14, No. 6: 248-250, Jun. 1998).*
Smith et al (Nature Biotechnology 15:1222-1223, Nov. 1997.*
, Brenner (TIG 15, 4:132-133, Apr. 1999).*
Borks (TIG 12, 10:425-427, Oct. 1996).*
(Ahlquist, RNA silencing and noncoding RNA. Science 296, pp. 1270-1273, May 2002.*
Schiebel, et al, Isolation of an RNA-Directed RNA polymerase-specific cDNA clone from tomato, Plant Cell, vol. 10, Dec. 1998, pp. 2087-2101.*

SEQ ID No.: 1 of US Patent 5,498,533. issued Mar. 12, 1996, has a 29 bp identity with SEQ ID No.: 1 of instant case.*
Maniatis, et. al. Molecualr Cloning, a Laboratory Manual, 1982, Cold Spring Harbor Laboratory, pp. 388-389).*
Amasino, R. Analytical Biochemistry 152: 304-307 (1986).*
Kull et al. Journal of Genetics and Breeding 49(1): 69-76 (Mar. 1995).*
Stam et al. Annals of Botany 79: 3-12 (1997).*
David C. Baulcombe, "Mechanisms of Pathogen-Derived Resistance to Viruses in Transgenic Plants", *The Plant Cell*, vol. 8. pp. 1833-1844 (Oct. 1996).
David C. Baulcombe, "RNA as a Target and an Initiator of Post-Transcriptional Gene Silencing in Trangenic Plants", *Plant Molecular Biology*, vol. 32, pp. 79-88 (1996).
David C. Baulcombe et al., "Ectopic Pairing of Homologous DNA and Post-Transcriptional Gene Silencing in Transgenic Plants", *Current Opinion in Biotechnology*, vol. 7, pp. 173-180 (1996).
Frank Boege et al., "In Vitro Transcription of Viroid RNA into Full-Length Copies by RNA-Dependent RNA Polymerase from Healthy Tomato Leaf Tissue", *Bioscience Reports*, vol. 2, pp. 185-194 (1982).
Frank Boege, "Simultaneous Presence of Terminal Adenylyl, Cytidylyl, Guanylyl, and Uridylyl Transferase in Healthy Tomato Leaf Tissue: Separation from RNA-Dependent RNA Polymerase and Characterization of the Terminal Transferases", *Bioscience Reports*, vol. 2, pp. 379-389 (1982).
Frank Boege et al., "RNA-Dependent RNA Polymerase from Healthy Tomato Leaf Tissue", *FEBS Letters*, vol. 121(1), pp. 91-96 (Nov. 1980).

(Continued)

*Primary Examiner*—David T. Fox
(74) *Attorney, Agent, or Firm*—Kathleen D. Rigaut; Dann Dorfman Herell & Skillman, P.C.

(57) ABSTRACT

Described are nucleic acid molecules encoding polypeptides having the enzymatic activity of an RNA-directed RNA polymerase (RdRP). Vectors comprising said nucleic acid molecules, wherein the nucleic acid molecules are operatively linked to regulatory elements allowing expression In prokaryotic and/or eukaryotic host cells are provided. Additionally, polypeptides encoded by said nucleic acid molecules and methods for the production of said polypeptides are described. Described are also pharmaceutical and diagnostic compositions as well as kits comprising the aforementioned nucleic acid molecules and/or comprising a nucleic acid molecule which is complementary to such a nucleic acid molecule. Said compositions and kits may further comprise polypeptides encoded by the described nucleic acid molecules. Furthermore, antagonists and inhibitors of the aforesaid polypeptides and/or antibodies specifically recognizing such polypeptides are described. Also provided are methods and uses comprising the nucleic acid molecules, vectors, polypeptides, antibodies and antagonists and inhibitors of the invention for modulating gene expression In humans and animals. Furthermore, transgenic plant cells and plants containing the aforementioned nucleic acid molecules as well as the use of the aforementioned nucleic acid molecules, polypeptides and/or antagonists/inhibitors in plant cell culture and plant tissue culture and/or plant breeding are described.

15 Claims, 6 Drawing Sheets

OTHER PUBLICATIONS

Carlo Cogoni et al., "Conservation of Transgene-Induced Post-Transcriptional Gene Silencing in Plants and Fungi", *Trends in Plant Science*, vol. 2(11), pp. 438-443 (Nov. 1997).

C. Cogoni et al. "Gene Silencing in *Neurospora crassa* Requires a Protein Homologous to RNA-Dependent RNA Polymerase," *Nature* 399: 166-169 (1999).

William O. Dawson, "Gene Silencing and Virus Resistance: a Common Mechanism", *Trends in Plant Science*, vol. 1(4), pp. 107-108 (Apr. 1996).

Ann Depicker et al., "Post-Transcriptional Gene Silencing in Plants", *Current Opinion in Cell Biology*, vol. 9, pp. 373-382 (1997).

William G. Dougherty et al., "Transgenes and Gene Suppression: Telling Us Something New?", *Current Opinion in Cell Biology*, vol. 7, pp. 399-405 (1995).

C.T. Duda, "Synthesis of Double-Stranded RNA: II. Partial Purification and Characterization of an RNA-Dependent RNA Polymerase in Healthy Tobacco Leaves", *Virology*, vol. 92, pp. 180-190 (1979).

C.T. Duda et al., "*In Vitro* Synthesis of Double-Stranded RNA by an Enzyme System Isolated from Tobacco Leaves", *Biochim Biophys Acta*, vol. 319(1), pp. 62-71 (Aug. 1973).

Taline Elmayan et al., "Expression of Single Copies of a Strongly Expressed 35S Transgene Can Be Silenced Post-Transcriptionally", *The Plant Journal*, vol. 9(6), pp. 787-797 (1996).

James J. English et al., "Requirement of Sense Transcription for Homology-Dependent Virus Resistance and *Trans*-Inactivation", *The Plant Journal*, vol. 12(3), pp. 597-603 (1997).

James J. English et al., "Suppression of Virus Accumulation in Transgenic Plants Exhibiting Silencing of Nuclear Genes", *The Plant Cell*, vol. 8, pp. 179-188 (Feb. 1996).

D.M.A. Evans et al., "Characterization of RNA-Dependent RNA Polymerases in Healthy and Tobacco Mosaic Virus-Infected Tomato Plants", *Annals of Botany*, vol. 54, pp. 271-281 (1984).

A. Fire, "RNA-Triggered Gene Silencing," *Trends in Genetics* 15: 358-363 (1999).

R.B. Flavell, "Inactivation of Gene Expression in Plants as a Consequence of Specific Sequence Duplication", *Proc. Natl. Acad. Sci. USA*, vol. 91, pp. 3490-3496 (Apr. 1994).

R.B. Flavell et al., "Development Regulation of Co-Suppression in *Petunia hybrida*", *Curr. Top. Microbiol. Immunol.*, vol. 197, pp. 43-56 (Jan. 1995).

Heinz Fraenkel-Conrat, "RNA-Directed RNA Polymerases of Plants", *CRC Critical Reviews in Plant Sciences*, vol. 4(3), pp. 213-226 (1986).

H. Fraenkel-Conrat, "RNA-Dependent RNA Polymerases of Plants", *Proc. Natl. Acad. Sci. USA*, vol. 80, pp. 422-424 (Jan. 1983).

Bernd Haas et al., "The Use of Synthetic Oligo-RNA and -DNA as Defined Templates for the Determination of Catalytic Properties of RNA-Directed RNA Polymerase from Tomato Leaf Tissue", *Nucleosides & Nucleotides*, vol. 7(5&6), pp. 713-716 (1988).

Masato Ikegami et al., "Characterization of the RNA-Dependent RNA Polymerase of Tobacco Leaves", *The Journal of Biological Chemistry*, vol. 254(1), pp. 149-154 (Jan. 1979).

Richard Jorgensen, "Developmental Significance of Epigenetic Impositions on the Plant Genome: A Paragenetic Function for Chromosomes", *Developmental Genetics*, vol. 15, pp. 523-532 (1994).

Richard A. Jorgensen, "Cosuppression, Flower Color Patterns, and Metastable Gene Expression States", *Science*, vol. 268, pp. 686-691 (May 1995).

Z.A. Khan et al., "RNA-Directed RNA Polymerases from Healthy and from Virus-Infected Cucumber", *Proc. Natl. Acad. Sci. USA*, vol. 83, pp. 2383-2386 (Apr. 1986).

J.A. Kooter et al. "Listening to the Silent Genes: Transgene Silencing, Gene Regulation and Pathogen Control," *Trends in Plant Science* 4: 340-347 (1999).

Christian Kunz et al., "Developmentally Regulated Silencing and Reactivation of Tobacco Chitinase Transgene Expression", *The Plant Journal*, vol. 10(3), pp. 437-450 (1996).

John A. Lindbo et al., "Induction of a Highly Specific Antiviral State in Transgenic Plants: Implications for Regulation of Gene Expression and Virus Resistance", *The Plant Cell*, vol. 5, pp. 1749-1759 (Dec. 1993).

B. Gregory Louis et al., "Purification and Properties of the Ribonucleic Acid-Dependent Ribonucleic Acid Polymerase from *Halobacterium cutirubrum*", *Biochem. J.*, vol. 128, pp. 755-762 (1972).

Marjori A. Matzke et al., "How and Why Do Plants Inactivate Homologous (Trans)genes?", *Plant Physiol.*, vol. 107, pp. 679-685 (1995).

Peter Meyer, "Understanding and Controlling Transgene Expression", *TIBTECH*, vol. 13, pp. 332-337 (Sep. 1995).

P. Meyer et al., "Homology-Dependent Gene Silencing in Plants", *Annu. Rev. Plant Physiol. Plant Mol. Biol.*, vol. 47, pp. 23-48 (1996).

M. Prins et al., "RNA-Mediated Virus Resistance in Transgenic Plants", *Arch. Virol.*, vol. 141, pp. 2259-2276 (1996).

C.P. Romaine et al., "RNA-Dependent RNA Polymerases in Uninfected and Tobacco Mosaic Virus-Infected Tobacco Leaves: Viral-Induced Stimulation of a Host Polymerase Activity", *Virology*, vol. 86, pp. 241-253 (1978).

H.L. Sänger et al., "The Possible Links between RNA-Directed DNA Methylation (RdDM), Sense and Antisense RNA, Gene Silencing, Symptom-Induction upon Microbial Infections and RNA-Directed RNA Polymerase (RDRP)", *Proceedings from the 8th International Symposium on Molecular Plant-Microbe Interactions Knoxville, Tennessee*, pp. 1-8 (Jul. 14-19, 1996).

Winfried Schiebel et al., "RNA-Directed RNA Polymerase from Tomato Leaves: I. Purification and Physical Properties", *The Journal of Biological Chemistry*, vol. 263(16), pp. 11851-11857 (1993).

Winfried Schiebel et al., "RNA-Directed RNA Polymerase from Tomato Leaves: II. Catalytic *In Vitro* Properties", *The Journal of Biological Chemistry*, vol. 268(16), pp. 11858-11867 (1993).

W. Schiebel et al. "Isolation of an RNA-Directed RNA Polymerase-Specific cDNA Clone from Tomato" *The Plant Cell* 10: 2087-2101 (1998).

Titia Sijen et al., "RNA-Mediated Virus Resistance: Role of Repeated Transgenes and Delineation of Targeted Regions", *The Plant Cell*, vol. 8, pp. 2277-2294 (Dec. 1996).

Holly A. Smith et al., "Transgenic Plant Virus Resistance Mediated by Untranslatable Sense RNAs: Expression, Regulation, and Fate of Nonessential RNAs", *The Plant Cell*, vol. 6, pp. 1441-1453 (Oct. 1994).

Maike Stam et al., "The Silence of Genes in Transgenic Plants", *Annals of Botany*, vol. 79, pp. 3-12 (1997).

Maike Stam et al., "Post-Transcriptional Silencing of Chalcone Synthase in *Pentunia* by Inverted Transgene Repeats", *The Plant Journal*, vol. 12(1), pp. 63-82 (1997).

Yoichi Takanami et al., "Comparative Studies on Ribonucleic Acid Dependent RNA Polymerases in Cucumber Mosaic Virus Infected Cucumber and Tobacco and Uninfected Tobacco Plants", *Biochemistry*, vol. 21, pp. 3161-3167 (1982).

Crispin B. Taylor, "Comprehending Cosuppression", *The Plant Cell*, vol. 9, pp. 1245-1249 (Aug. 1997).

Helena Van Houdt et al., "Post-Transcriptional Silencing of a Neomycin Phosphotransferase II Transgene Correlates with the Accumulation of Unproductive RNAs and with Increased Cytosine Methylation of 3' Flanking Regions", *The Plant Journal*, vol. 12(2), pp. 379-392 (1997).

Vladimir Volloch et al., "Antisense Globin RNA in Mouse Erythroid Tissues: Structure, Origin, and Possible Function", *Proc. Nat. Acad. Sci.*, vol. 93, pp. 2476-2481 (Mar. 1996).

M. Wassenegger "RNA-directed RNA Polymerase (RdRP) as a Possible Enzyme for *In Vitro* Synthesis of 'Antisense'RNA," *9. Tagung, Molekularbiologie der Pflanzen* at Werningerode, Germany (Mar. 5 to 8, 1996).

Milton Zaitlin et al., "Plant Virus-Host Interactions", *Ann. Rev. Plant Physiol.*, vol. 38, pp. 291-315 (1987).

Zhixin Xie et al., "An Important Role of an Inducible RNA-Dependent RNA Polymerase in Plant Antiviral Defense," *Proc. Nat. Acad. Sci. USA* vol. 98, pp. 6516-6520 (May 22, 2001).

* cited by examiner

Southern analysis of genomic tomato DNA.

Southern analysis of different genomic DNAs.

Northern analysis of total tomato RNA

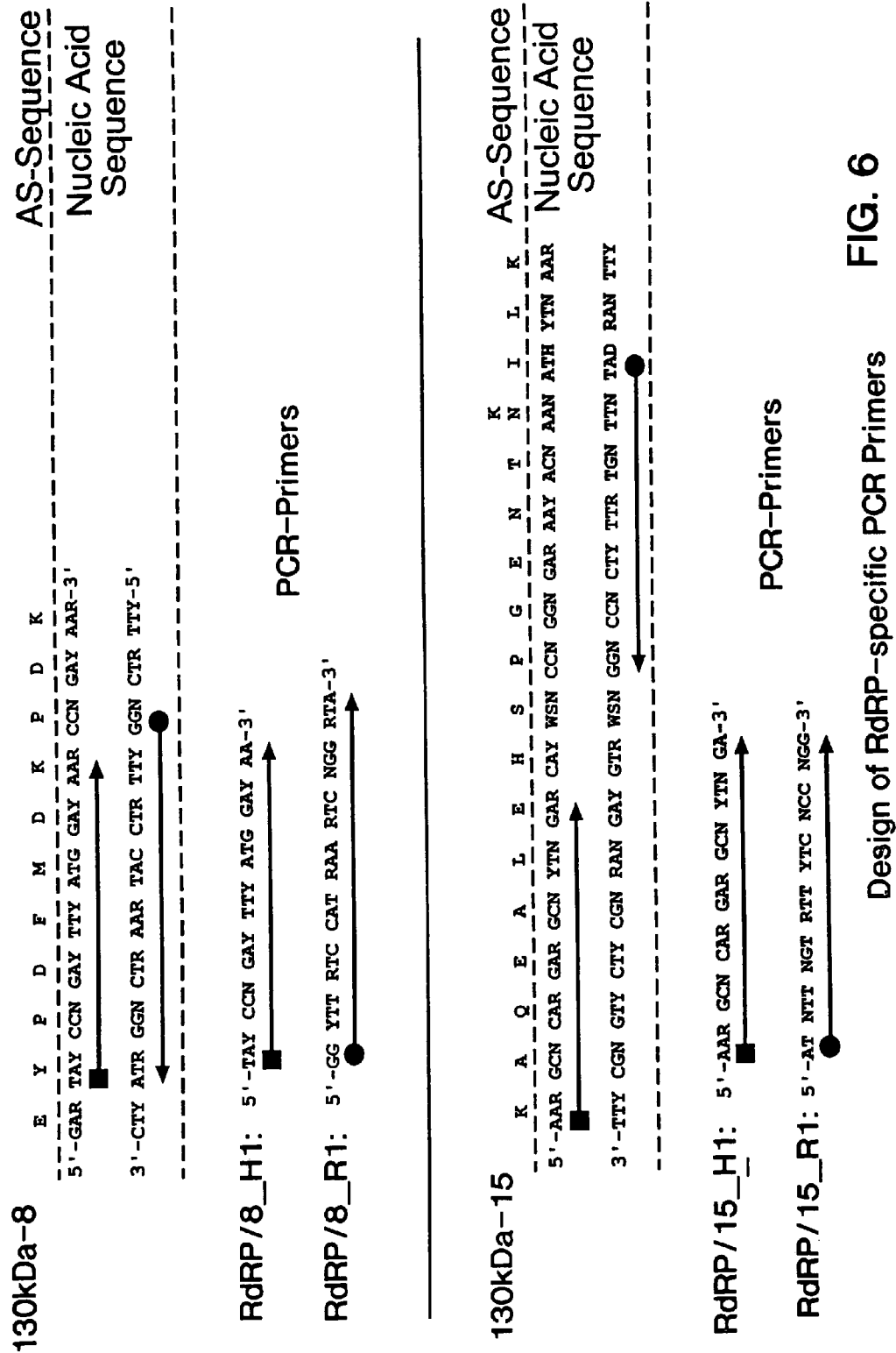
FIG. 6  Design of RdRP-specific PCR Primers

NUCLEIC ACID MOLECULES ENCODING POLYPEPTIDES HAVING THE ENZYMATIC ACTIVITY OF AN RNA-DIRECTED RNA POLYMERASE (RDRP)

This application is a divisional of U.S. application Ser. No. 08/811,583 filed 05 Mar. 1997, now U.S. Pat. No. 6,218,142.

SUMMARY OF THE INVENTION

The present invention relates to nucleic acid molecules encoding polypeptides having the enzymatic activity of an RNA-directed RNA polymerase (RdRP). The present invention also provides vectors comprising said nucleic acid molecules, wherein the nucleic acid molecules are operatively linked to regulatory elements allowing expression in prokaryotic and/or eukaryotic host cells. Additionally, the present invention relates to polypeptides encoded by said nucleic acid molecules and methods for the production of said polypeptides. The present invention further relates to pharmaceutical and diagnostic compositions as well as kits comprising the aforementioned nucleic acid molecules and/or comprising a nucleic acid molecule which is complementary to such a nucleic acid molecule. Said compositions and kits may further comprise polypeptides encoded by the described nucleic acid molecules. Furthermore, the present invention relates to antagonists and inhibitors of the aforesaid polypeptides and/or antibodies specifically recognizing such polypeptides. Also within the scope of the present invention are methods and uses comprising the nucleic acid molecules, vectors, polypeptides, antibodies and antagonists and inhibitors of the invention for modulating gene expression in humans and animals. Furthermore, the present invention relates to transgenic plant cells and plants containing the aforementioned nucleic acid molecules as well as the use of the aforementioned nucleic acid molecules, polypeptides and/or antagonists/inhibitors in plant cell culture and plant tissue culture and/or plant breeding.

BACKGROUND OF THE INVENTION

Since the development of plant transformation systems a particular interest exists on the stable expression of foreign genes in higher plants. Although these attempts were successfully realized for several herbicide resistance genes, a series of experiments failed that had been designed to use plants as efficient bio-reactors. It seemed that higher plants have a system of defense to protect themselves against overexpression of foreign genes. Whenever a transgene expression comes up to a threshold dose it is without selective pressure silenced either by transcriptional or post-transcriptional inactivation. Recent studies on these phenomena indicated that "antisense" RNA might be responsible for these silencing mechanisms. The idea of an "antisense" RNA-mediated gene silencing was substantiated by the analysis of transgenically mediated virus resistance in plants (Smith et al., 1994; English et al., 1996; Sijen et al., 1996). It could be shown that the in vivo transcripts of non-translatable "sense" cDNA constructs which had been integrated into the plant genome can mediate resistance against Infection with plant viruses. Further analysis revealed that this resistance which was due to post-transcriptional gene silencing (PTGS) only occurred when the transgene shared homology with the Infecting virus. Based on these data and with regard to previous results describing the co-suppression phenomena in plants (for review see Meyer, 1996) several models explaining the PTGS mechanism have been introduced (English et al., 1996; Baulcomb, 1996; Sijen et al., 1996). Common to all these models is the assumption that "antisense" RNAs are synthesized from "sense" RNA templates by an RNA-directed RNA polymerase (RdRP). Subsequently the produced "antisense" RNAs can hybridize to complementary parts of mRNAs or invading virus RNAs which would unresistingly lead to degradation of the double-stranded regions.

It is most likely that this PTGS is not restricted to transgenes but that it is also involved in normal plant gene regulation. Moreover, it is most likely that the same mechanism takes place in all higher eukaryots. Therefore, a detailed examination of RNA-mediated gene regulation had become an important aspect of basic and applied research. An RNA-dependent RNA polymerase (EC 2.7.7.48, RdRP) activity has been detected in healthy plant tissue, for review see Fraenkel-Conrat (1986). Previous studies of RdRP activity have suffered from the inhomogeneity of enzyme preparations and of the resulting RNA products in that they did not allow the precise determination of their template complementarity by direct RNA sequencing. Schiebel et al. (1993 a, b) provided evidence for the concept that the RdRP mediated transcription is a truly RNA-instructed process yielding products that are precise complementary copies of the RNA template offered to an RdRP active enzyme preparation. However, although purification of the RdRP from tomato leaf tissue to electrophoretic homogeneity was reported (Schiebel et al., 1993 a, b), the enzyme preparations were not approachable for amino acid sequencing. One reason for the slow progress in elucidating the amino acid sequence of the RdRP is to be seen in the fact that only low amounts of protein could be isolated using the hitherto available technology and/or that there existed further proteins in the enzyme preparations obtainable with standard techniques which resulted in non-informative or even false sequence information. However, for efficient use of RdRP associated technology, it was desirable to be able to manipulate the genetic material associated with said technology.

Thus, the technical problem underlying the present invention is to provide such material.

DETAILED DESCRIPTION OF THE INVENTION

The solution to the technical problem is achieved by providing the embodiments characterized in the claims.

Accordingly, the invention relates to a nucleic acid molecule encoding a polypeptide having the enzymatic activity of an RNA-directed RNA polymerase (RdRP) or encoding an enzymatically active fragment thereof selected from the group consisting of:

(a) nucleic acid molecules encoding a polypeptide comprising the amino acid sequence given in SEQ ID NO:2;

(b) nucleic acid molecules comprising the nucleotide sequence given in SEQ ID NO:1;

(c) nucleic acid molecules hybridizing with a complementary strand of a nucleic acid molecule as defined in (a) or (b); and (d) nucleic acid molecules, the nucleotide sequence of which is degenerate as a result of the genetic code to a nucleotide sequence of a nucleic acid molecule as defined in (c).

In accordance with the present invention, a nucleic acid molecule encoding a novel class of RdRPs has been identified. This has been achieved by using a novel purification method for the isolation of a polypeptide having the enzymatic activity of an RdRP which was suitable for amino acid sequencing. Oligonucleotides were designed and used for cloning of the corresponding cDNA.

The polypeptide encoded by the nucleic acid sequence of SEQ ID NO: 1 from nucleotide 194 to nucleotide 3535 encodes a polypeptide of a 1114 amino acids with a calculated molecular weight of about 127 kDa. This data is in good agreement with the prior art experimental values that had been determined by SDS-PAGE (128 kD) and sucrose gradient centrifugation (119 kD) (Schiebel et al., 1993a). The nucleotide and the amino acid sequence given in SEQ ID NOS: 1 and 2, respectively, displayed no significant homologies to sequences in any database (Blast X, GAP, Wisconsin Sequence Packaging System, Version 7.0) searched. In addition, the presence of putative phosphorylation sites for putative protein kinases can be identified by computer aided search for phosphorylation consensus sequences which suggests possible regulation by phosphorylation. Studies which had been carried out in accordance with the present invention revealed that the polypeptide encoded by the nucleotide sequence of SEQ ID NO:1 is identical with the RdRP isolated from tomato plants as described in example 1 of the present application.

The polypeptide encoded by the nucleotide sequence of SEQ ID NO:1 displays the ability to catalyze in vitro transcription of preferably short single-stranded RNA and DNA molecules into precisely complementary RNA copies up to the full length of these templates. The RdRP-directed transcription can be primed by RNA and DNA oligonucleotides complementary to the 3'-terminal nucleotides of the template. In addition, the RdRP encoded by the nucleic acid molecule of the invention can catalyze unprimed transcription. An unprimed transcription starts preferentially at the 3'-terminal nucleotides of a corresponding template. Furthermore, the RdRP is capable of adding a single non-complementary nucleotide to the 3' terminus; see also Schiebel et al. (1993b).

The term "RNA-directed RNA polymerase" (RdRP), as used herein, means that said polypeptide or enzymatically active fragment thereof is capable of RNA-directed RNA synthesis, thus using RNA as a template for synthesizing complementary RNA molecules. However, as set forth above, said RdRP may also be capable of accepting single-stranded DNA molecules as templates for RNA transcription.

The availability of the nucleic acid molecules encoding the RdRP is definitely a major advantage because now experiments are possible that allow both the "knock-out" and the improvement of the regulation mechanism for a given gene.

The nucleotide sequence depicted in SEQ ID NO: 1, in general, encodes a novel class of polypeptides having RdRP activity. By the provision of this nucleotide sequence, it is now possible to isolate identical or homologous nucleic acid molecules which encode polypeptides with the enzymatic activity of said polypeptide from other species or organisms.

Thus, the invention also relates to nucleic acid molecules hybridizing with the above-described nucleic acid molecules and differ in one or more positions in comparison with these as long as they encode a polypeptide having RdRP activity. Such molecules comprise those which are altered, for example, by deletion(s), insertion(s), substitution(s), addition(s) and/or recombination(s) or any other modification(s) known in the art either alone or in combination in comparison to the above-described nucleic acid molecules. Methods for introducing such modifications in the nucleic acid molecules according to the invention are well-known to the person skilled in the art. The invention also relates to nucleic acid molecules the sequence of which differs from the nucleotide sequence of any of the above-described nucleic acid molecules due to the degeneracy of the genetic code.

By "hybridizing" it is meant that such nucleic acid molecules hybridize under conventional hybridization conditions, preferably under stringent conditions such as described by, e.g., Sambrook et al. (Molecular Cloning; A Laboratory Manual, 2nd Edition, Cold Spring Harbor Laboratory Press, Cold Spring Harbor, N.Y. (1989)).

In a preferred embodiment the nucleic acid molecules according to the invention are RNA or DNA molecules, and most preferably cDNA or genomic DNA. It should also be understood that the nucleic acid molecules of the invention may be synthetically synthesized DNA or RNA molecules or hybrids thereof. Preferably, said nucleic acid molecules may be prepared from nucleic acids obtained from any organism, tissue or cell, namely from bacteria. eucaryotes or archaebacteria and preferably from mammalian, plant, insect, bacterial, or fungal cells, worm cells such as derived from C. elegans or viruses. In a further most preferred embodiment the nucleic acid molecule of the invention is derived from a plant, preferably from tomato.

Nucleic acid molecules hybridizing with the above-described nucleic acid molecules can, in general, be derived from any organism comprising such molecules, preferably from monocotyledonous or dicotyledonous plants, in particular from any plant of interest in agriculture, horticulture or wood culture, such as crop plants, namely those of the family Poaceae, any other starch producing plants, such as potato, maniok, leguminous plants, oil producing plants, such as oilseed rape, linenseed, etc., plants using polypeptide as storage substances, such as soybean, plants using sucrose as storage substance, such as sugar beet or sugar cane, trees, ornamental plants etc. Preferably the nucleic acid molecules according to the invention are derived from plants belonging to the family Solanaceae. Identical or similar polypeptides may also be found in animals, preferably mammals. Nucleic acid molecules hybridizing to the above-described nucleic acid molecules can be isolated, e.g., form libraries, such as cDNA or genomic libraries by techniques well known in the art. For example, hybridizing nucleic acid molecules can be identified and isolated by using the above-described nucleic acid molecules or fragments thereof or complementary sequences thereof as probes to screen libraries according to standard techniques. Possible is also the isolation of such nucleic acid molecules by applying the polymerase chain reaction (PCR) using as primer oligonucleotides derived form the above-described nucleic acid molecules.

Nucleic acid molecules which hybridize with any of the aforementioned nucleic acid molecules also include fragments, derivatives and allelic variants of the above-described nucleic acid molecules that encode a polypeptide having RdRP activity or a enzymatically active fragment thereof. Fragments are understood to be parts of nucleic acid molecules long enough to encode the described polypeptide or an enzymatically active fragment thereof. The term "derivative" means in this context that the nucleotide sequence of these nucleic acid molecules differs from the sequences of the above-described nucleic acid molecules in one or more nucleotide positions and homologous to said nucleic acid molecules. Homology is understood to refer to a sequence identity of at least 40%, particularly an identity of at least 60%, preferably more than 80% and still more preferably more than 90%. The deviations from the sequences of the nucleic acid molecules described above can, for example, be the result of substitution(s), deletion(s), addition(s), insertion(s) and/or recombination(s) either alone or in combination.

Homology further means that the respective nucleic acid molecules or encoded polypeptides are enzymatically and/or structurally equivalent. The nucleic acid molecules that are homologous to the nucleic acid molecules described above and that are derivatives of said nucleic acid molecules are, for example, by way of variations of said nucleic acid molecules which represent modifications having the same enzymatic function. They may be naturally occurring variants, such as sequences from other plant varieties or species, or obtained by mutation. These mutations may occur naturally or may be obtained by mutagenesis techniques. The allelic variants may be naturally occurring allelic variants as well as synthetically produced or genetically engineered variants.

The polypeptides encoded by the various derivatives and variants of the above-described nucleic acid molecules share one or several specific common characteristics, such as enzymatic activity, molecular weight, immunological reactivity, conformation, etc., as well as physical properties, such as electrophoretic mobility, chromatographic behavior, sedimentation coefficients, pH optimum, temperature optimum, stability, solubility, spectroscopic properties, etc.

All such fragments, variants and derivatives of the RdRP of the invention are included within the scope of this invention, as long as the essential characteristic RdRP activity as defined above remains unaffected in kind.

In a further embodiment, the invention relates to nucleic acid molecules of at least 15 nucleotides in length hybridizing specifically with a nucleic acid molecule as described above or with a complementary strand thereof. This means that they hybridize, preferably under stringent conditions, specifically with the nucleic acid molecules as described above and show no or very little cross-hybridization with nucleic acid molecules encoding other polypeptides. Such nucleic acid molecules may be used as probes and/or for the control of gene expression. Nucleic acid probe technology is well known to those skilled in the art who will readily appreciate that such probes may vary in length. The nucleic acid probes of the invention are useful for various applications. On the one hand, they may be used as PCR primers for amplification of nucleic acid molecules according to the invention. On the other hand, they can be useful tools for the detection of the expression of nucleic acid molecules according to the invention in plants or any other organism, for example mammals, by e.g. in-situ hybridization or Northern-Blot hybridization. Another application is the use as a hybridization probe to identify nucleic acid molecules hybridizing to the nucleic acid molecules according to the invention by homology screening of genomic or cDNA libraries. Nucleic acid molecules according to this preferred embodiment of the invention which are complementary to a nucleic acid molecule as described above may also be used for repression of expression of a nucleic acid molecule encoding a polypeptide having RdRP activity, for example due to an antisense effect or for the construction of appropriate ribozymes which specifically cleave such nucleic acid molecules. Furthermore, the person skilled in the art is well aware that it is also possible to label such a nucleic acid probe with an appropriate marker for specific applications, such as for the detection of the presence of a nucleic acid molecule of the invention in a sample derived from an organism.

The present invention also relates to vectors, particularly plasmids, cosmids, viruses, bacteriophages used conventionally in genetic engineering that contain a nucleic acid molecule according to the invention.

In a preferred embodiment the nucleic acid molecule present in the vector is linked to regulatory elements which allow the expression of the nucleic acid molecule in prokaryotic and/or eukaryotic cells. The nucleic acid molecule encoding the polypeptide having RdRP activity and the template nucleic acid molecule may be contained in different or in the same vector. Expression comprises transcription of the nucleic acid molecule, preferably into a translatable mRNA. Regulatory elements ensuring expression in prokaryotic and/or eukaryotic calls are well known to those skilled in the art. In the case of eukaryotic cells they normally comprise promoters ensuring initiation of transcription and optionally poly-A signals ensuring termination of transcription and stabilization of the transcript. Additional regulatory elements may include transcriptional as well as translational enhancers.

The present invention furthermore relates to host cells comprising a vector as described above or a nucleic acid molecule according to the invention wherein the nucleic acid molecule is foreign to the host cell.

By "foreign" it is meant that the nucleic acid molecule is either heterologous with respect to the host cell which means that said nucleic acid molecule is derived from a cell or organism with a different genomic background, or that is homologous with respect to the host cell but located in a different genomic environment than the naturally occurring counterpart of said nucleic acid molecule. This means that, if the nucleic acid molecule is homologous with respect to the host cell, it is not located in its natural location in the genome of said host cell. In this case the nucleic acid molecule may be either under the control of its own promoter or under the control of a heterologous promoter. The vector or nucleic acid molecule according to the invention which is present in the host cell may either be integrated into the genome of the host cell or it may be maintained extrachromosomally. In this respect, it is also to be understood that the nucleic acid molecule of the invention can be used for "gene targeting" and/or "gene replacement", for restoring a mutant gene or for creating a mutant gene via homologous recombination.

The host cell can be any prokaryotic or eukaryotic cell, such as a bacterial, insect, fungal, worm, plant or animal cell. Preferred fungal cells are, for example, those of the genus Saccharomyces, in particular those of the species *S. cerevisiae*.

Another object of the invention is a method for the preparation of such polypeptides encoded by the nucleic acid sequence of the invention which comprises the cultivation of host cells according to the invention which, due to the presence of a vector or a nucleic acid molecule according to the invention, are able to express such a nucleic acid molecule, under conditions which allow expression of the nucleic acid molecule and recovering of the so-produced polypeptide from the culture. Depending on the specific constructs and conditions used, the polypeptide may be recovered from the cells, from the culture medium or from both. For the person skilled in the art it is well known that it is not only possible to have as an expression product a native polypeptide but also to obtain the polypeptide as a fusion polypeptide or to add signal sequences directing the polypeptide to specific compartments of the host cell, ensuring secretion of the polypeptide into the culture medium, etc.

The present invention furthermore relates to polypeptides encoded by the nucleic acid molecules according to the invention or produced by the above-described method, and to enzymatically active fragments of such polypeptides having RdRP activity. In this context, it is also understood that the polypeptides according to the invention may be further modified by conventional methods known in the art. For example, such a polypeptide or fragment thereof can be chemically modified according to standard methods. By providing the polypeptides according to the present invention it is also possible to determine fragments which retain enzymatic activity, namely the capability of RNA-directed RNA synthesis as defined in this specification. This allows the construction of chimeric proteins and polypeptides comprising at least part of the amino sequence of the polypeptide of the invention, which is crucial for RdRP activity and other functional amino acid sequences. The other functional amino acid sequence(s) may be either physically linked by, e.g., chemical means to the polypeptide of the invention or to an enzymatically active part thereof or may be fused by recombinant DNA techniques well known in the art.

In a preferred embodiment the above-described polypeptide or fragment is phosphorylated. As set forth above, the amino acid sequence of the polypeptide of the invention may be phosphorylated due to the presence of possible phosphorylation sites. Thus, it may be possible to regulate the function of said polypeptide by phosphorylation. Phosphorylation of the polypeptide of the invention may be effected in vivo in the host which expresses said polypeptide or in vitro by, for example, bringing an appropriate protein kinase in contact with said polypeptide or fragment.

Furthermore, the present invention relates to antibodies specifically recognizing polypeptides according to the invention or parts, i.e. specific fragments or epitopes, of such polypeptides. Specific epitopes or fragments may, for example, comprise amino acid sequences which constitute domains which are characteristic for the polypeptides according to the invention, such as described in the appended examples.

These antibodies can be monoclonal antibodies, polygonal antibodies or synthetic antibodies as well as fragments of antibodies, such as Fab, Fv, or scFv fragments etc. These antibodies or fragments thereof can be used, for example, for the immunoprecipitation and immunolocalization of polypeptides according to the invention as well as for the monitoring of the synthesis of such polypeptides, for example, in recombinant organisms, and for the identification of polypeptides interacting with the polypeptides according to the invention. They can further be employed in the screening of expression libraries.

Moreover, the present invention relates to an antagonist/inhibitor of the polypeptide of the invention. Potential antagonists are, for example, oligonucleotides or antibodies which bind to a nucleic acid molecule or polypeptide of the invention, respectively, such that either the expression of the nucleic acid molecule encoding a polypeptide of the invention or the RdRP activity of the polypeptide of the invention is prevented. Potential antagonists also include antisense constructs prepared through the use of antisense technology. Another potential antagonist is a small molecule which binds to the catalytic or to a regulatory portion of the polypeptide of the invention such that normal enzymatic activity is prevented. Examples of small molecules include, but are not limited to nucleotide analogs, small polypeptides or peptide-like molecules or any combinations thereof. Such antagonists may be identified by using the nucleic acid molecules, vectors and polypeptides of the invention.

Thus, in a further embodiment the present invention relates to a method for identifying an antagonist/inhibitor of the polypeptide of the invention comprising:
(a) contacting the polypeptide of the invention with a plurality of compounds to be screened;
(b) determining whether said polypeptide is still capable of RNA-directed RNA synthesis; and
(c) identifying the compound which inhibits the RNA-directed RNA synthesis.

Said plurality of compounds may be comprised in, for example, cell extracts from, e.g. plants or microorganisms. Furthermore, said compounds may be known in the art but hitherto not known to be an activator/inhibitor of the polypeptide of the invention. In the later case, the method would comprise the following steps:
(a) contacting the polypeptide of the invention with a compound to be tested;
(b) determining whether said polypeptide is still capable of RNA-directed RNA synthesis.

As discussed in the background section of the description of the present invention, the RdRP synthesizes "antisense" RNAs from "sense" RNA-templates. Said "antisense" RNAs can hybridize to complementary parts of mRNAs or invading virus RNAs, which would lead to degradation of the so formed double-stranded regions. Furthermore, said "antisense RNAs" may bind to DNA, for example, via triple helix formation and thereby block gene expression. Thus, it is possible to suppress the expression of target nucleic acid molecules and preferably genes by introduction of template nucleic acid molecules transcribed by RdRP into host cells which either naturally express an RdRP or which were genetically engineered for the expression or overexpression of the polypeptide of the invention. The degree of "antisense" RNA production may depend on said template nucleic acid molecules in serving as an efficient template for the RdRP. With the aid of the RdRP of the present invention, it is now possible to determine the appropriate templates. Thus, in a further embodiment, the present invention relates to a method for determining whether a nucleic acid molecule is capable of serving as a template for RNA-directed RNA synthesis comprising:
(a) contacting the polypeptide of the invention with a preferably single stranded nucleic acid molecule; and
(b) determining whether the complementary strand of said nucleic acid molecule is synthesized.

The term "template" in the sense of the present invention relates to nucleic acid molecules of at least 15 nucleotides in length which are capable of serving as a template for the polypeptide of the invention. In other words said template can be transcribed into complementary RNA copies, preferably up to the full length of these templates. Said template nucleic acid molecule may be single stranded RNA or preferably single stranded DNA or a hybrid thereof. Furthermore, said template nucleic acid molecule may contain, for example, thioester bonds and/or nucleotide analogs commonly used in oligonucleotide antisense approaches. Such modifications may be useful for the stabilisation of the template nucleic acid molecule against endo- and/or exonucleases. The template nucleic acid molecules may also be transcribed by an appropriate vector containing a chimeric gene which allows for the transcription of a template RNA in prokaryotic and/or eukaryotic cell.

Moreover, the present invention relates to a pharmaceutical composition comprising at least one of the aforementioned nucleic acid molecules, vectors, polypeptides, antibodies and/or antagonists/inhibitors according to the invention either alone or in combination, and optionally a pharmaceutically acceptable carrier or excipient. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g. by intravenous, intraperitoneal, subcuteneous, intramuscular, topical or intradermal administration.

Although the RdRP-mechanism so far is only described for plants, it is now possible to employ the nucleic acid molecules, vectors and polypeptides of the invention for the suppression of undesired gene expression in humans and animals. For example, the possibility to express the RdRP in almost any organism opens up the chance to use this enzyme as a therapeutic agent for the control of, e.g., cancer and of virus infection in humans and animals. Even if a general RdRP-like mechanism is not restricted to plants, it is expected that enhancement of RNA-mediated gene silencing or suppression could suppress growth of those cells which show highly increased transcriptional activity. This enhancement can be achieved by introducing additional copies of the RdRP gene or by direct transfer of in vitro produced RdRP polypeptide, optionally together with a template nucleic acid molecule derived from the gene to be silenced or suppressed.

An additional medical application against undesired gene expression, e.g., virus infections and cancer is given when an active RdRP enzyme is produced in vitro. There are more and more attempts to cure virus infections and cancer with the aid of the "antisense" RNA-technique in that synthetic "antisense" oligonucleotides are injected into the corresponding cells. This therapy mainly depends on the choice of the oligonucleotide. It is hardly predictable whether chosen oligonucleotides are stable in the cytoplasm of the target cell and whether they are efficiently directed to an accessible region of the target RNA. Moreover high amounts of "antisense" RNAs have to be injected to ensure that the target RNA is completely degraded.

A more promising approach could be performed by activating the endogenous "RdRP-system" with appropriate "sense" RNA if such system exist in the organism. Following this approach there are major advantages. Useful "sense" nucleic acid molecules can be screened for by an in vitro RdRP assay as, for example, described above in that the suitability of said molecules in serving as an efficient template for the enzyme is analysed. If a suitable template is isolated, only low copy numbers of the template nucleic acid molecule have to be successfully transferred into the target cells. The endogenous RdRP should amplify the corresponding "antisense" RNA which will subsequently induce post transcriptional gene silencing.

The present invention also relates to diagnostic compositions or kits comprising at least one of the aforementioned nucleic acid molecules, vectors, polypeptides, antibodies and/or antagonists/inhibitors, and in the case of diagnostic compositions optionally suitable means for detection. The various compounds comprised in the kit and the diagnostic composition of the invention are preferably bottled in different containers.

Said diagnostic compositions may be used for methods for detecting expression of a polypeptide of the invention by detecting the presence of mRNA encoding a polypeptide having RdRP activity which comprises isolation of mRNA from a cell and contacting the mRNA so obtained with a probe comprising a nucleic acid probe as described above under hybridizing conditions, detecting the presence of mRNA hybridized to the probe, and thereby detecting the expression of the polypeptide by the cell.

Further methods of detecting the presence of a polypeptide according to the present invention comprises immuno-techniques well known in the art, for example enzyme linked immunosorbent assays.

Moreover, the present invention relates to the use of and methods employing a nucleic acid molecule, vector, and/or polypeptide of the invention and optionally or preferably a template nucleic acid molecule for treating a disease which is caused by the undesired expression or overexpression of a gene.

It is envisaged by the present invention that the nucleic acid molecules and polypeptides are administered either alone or in any combination, and optionally together with an appropriate RdRP template nucleic acid molecule described above, and/or together with a pharmaceutically acceptable carrier or excipient. Subsequent to administration, said nucleic acid molecules may be stably integrated into the genome of the mammal. On the other hand, viral vectors may be used which are specific for certain calls or tissues which persist in said cells thereby conferring expression of the nucleic acid molecules in said cells. Suitable pharmaceutical carriers and excipients are well known in the art. Elements capable of targeting a nucleic acid molecule and/or polypeptides to specific cells are described in the prior art, for example. Somia et al., Proc. Natl. Acad. Sci., USA 92 (1995). 7570–7574. The pharmaceutical compositions prepared according to the invention can be used for the prevention or treatment or delaying of different kinds of diseases, which are related to the expression or overexpression of a given gene or genes.

Furthermore, it is possible to use a pharmaceutical composition of the invention which comprises a nucleic acid molecule or vector of the invention, and optionally a template nucleic acid molecule in gene therapy. Naturally, both nucleic acid molecules may be also comprised in the same vector. For example, research pertaining to gene transfer into cells of the germ line is one of the fastest growing fields in reproductive biology. Gene therapy, which is based on introducing therapeutic genes into cells by ex-vivo or in-vivo techniques is one of the most important applications of gene transfer. Suitable vectors and methods for in-vitro or in-vivo gene therapy are described in the literature and are known to the person skilled in the art. The pharmaceutical compositions according to the invention can be used for the treatment of kinds of diseases hitherto unknown as being related to the expression and/or over expression of genes.

It is to be understood that the introduced nucleic acid molecules express an enzymatically active polypeptide of the invention after introduction into said cell and preferably remain in this status during the lifetime of said cell. On the other hand, the person skilled in the art may also use the nucleic acid molecules of the invention to "knock out" an endogenous gene encoding an RdRP, for example, by gene targeting or antisense or ribozyme technology.

In a further preferred embodiment of the method of the invention, said cell is a germ line cell or embryonic cell or derived therefrom. In a most preferred embodiment, said cell is an egg cell or derived therefrom.

In a further embodiment the invention relates to a method for treating a disease caused by the undesired expression or overexpression of a nucleic acid molecule comprising:
  (a) obtaining cells from a mammal;
  (b) introduction of a nucleic acid molecule or a vector of the invention and optionally a template nucleic acid molecule derived from said nucleic acid molecule which causes the disease into said cells; and (c) reintroducing the cells obtained as a product of step (b) into said mammal or into a mammal of the same species.

Said template nucleic acid molecule is preferably identified or determined by methods described hereinabove. Preferably, said mammal is a human, rat or mouse and/or the cell is a germ cell, an embryonic cell or an egg cell or a cell derived therefrom.

The present invention also relates to a method for the production of a transgenic mammal comprising introduction of a nucleic acid molecule or vector of the invention and optionally a template nucleic acid molecule into a germ cell, an embryonic cell or an egg or a cell derived therefrom. The invention also relates to transgenic animals obtained by said method.

Further, the present invention relates to transgenic mammalian cells, comprising stably integrated into the genome
(a) a nucleic acid molecule encoding a polypeptide of the invention, which is linked to regulatory elements allowing transcription and/or expression of the nucleic acid molecule in mammalian cells and/or
(b) a template nucleic acid molecule determined by the method of the invention which is linked to regulatory elements allowing transcription of said template nucleic acid molecule in mammalian cells.

In a further embodiment the invention relates to transgenic mammals comprising the above described mammalian cells.

In a further embodiment the present invention relates to a mammalian cell which contains stably integrated into the genome a nucleic acid molecule of the invention which is linked to regulatory elements allowing transcription of said nucleic acid molecule in mammalian cells wherein the presence of said nucleic acid molecule and/or the transcription and/or expression leads to reduction of the synthesis of the polypeptide of the invention in said cells.

In a preferred embodiment the reduction of the synthesis of the polypeptide of the invention in said cells is achieved by antisense, ribozyme and/or co-suppression effect. The present invention thus relates also to a transgenic mammal comprising such mammalian cells.

Preferably, the mammal referred to in the above embodiments is a human, a rat or a mouse.

Further embodiments and applications which also relate to the technology of transgenic mammals are discussed below with respect to transgenic plants. The person skilled in the art ia able to apply, where appropriate, the technologies and apllications discussed in connection with transgenic plants also to transgenic mammals.

The invention further relates to a transgenic plant cell comprising stably integrated into the genome
(a) a nucleic acid molecule of the invention which is linked to regulatory elements allowing transcription and/or expression of the nucleic acid molecule in plant cells and/or
(b) a template nucleic acid molecule determined by the method of the invention which is linked to regulatory elements allowing transcription of said template nucleic acid molecule in plant cells.

The nucleic acid molecules according to the invention are in particular useful for the genetic manipulation of plant cells in order to increase or decrease the RdRP activity in plants and by transferring the "RdRP-system" to organisms that lack a comparable mechanism to obtain plants with modified, preferably with improved or useful phenotypes.

For example, although a threefold increased concentration of the RdRP protein can be obtained by virus- or viroid-infection in tomato, the enzyme is still hardly detectable in those plants. Therefore it is expected that resistance of plants against RNA viruses can be improved by increasing the RdRP activity. For this purpose it is preferred to introduce at first a functional full-length RdRP cDNA copy into the genome of several crop plants. Regenerated transformants that have been screened for high RdRP activity have to be retransformed with a second construct to finally induce the RNA-mediated resistance against a particular virus. This transgene construct should provide in vivo transcripts which have to be homologous to a part of the virus RNA. In plants carrying both transgenes the improved resistance is based on the phenomenon that the increased RdRP activity leads to highly efficient production of "antisense" RNA. This would also include increased transcription of "antisense" RNAs from the nuclear-encoded virus-specific templates. These virus-specific "antisense" RNAs should be capable of inducing the sequence-specific RNA degradation process by hybridizing to the invading virus RNA.

The same gene silencing system could be applied to inactivate any endogenous gene in possibly all higher eukaryots. In case that an efficient RdRP activity can be introduced into a particular organism it should be possible to down-regulate genes by re- or cotransforming with transgene constructs that are encoding the corresponding RdRP templates.

Thus, the present invention relates also to transgenic plant or mammalian cells which contain stably integrated into the genome a nucleic acid molecule according to the invention linked to regulatory elements which allow for expression of the nucleic acid molecule in plant or mammalian cells and wherein the nucleic acid molecule is foreign to the transgenic plant or mammalian cell and optionally a template nucleic acid molecule. For the meaning of the term "foreign", we refer to our definition provided herein above.

Further, the present invention also relates to transgenic plants or mammalians comprising transgenic plant or mammalian cells according to the invention.

Furthermore, the invention relates to the transgenic plant cell which contains stably integrated into the genome a nucleic acid molecule according to the invention or part thereof, wherein the transcription and/or expression of the nucleic acid molecule or part thereof leads to reduction of the synthesis of a polypeptide having RdRP activity.

In a preferred embodiment, the reduction is achieved by an anti-sense, ribozyme and/or co-suppression effect.

The provision of the nucleic acid molecules according to the invention opens up the possibility to produce transgenic plant cells with a reduced level of the polypeptide as described above and, thus, inactivate antisense RNA production. Techniques how to achieve this are well known to the person skilled in the art. Experiments described in the prior art indicate that overexpressed transgenes as well as several tissue-specific or developmentally regulated endogenous plant genes can be post-transcriptionally silenced by the RdRP system. Therefore it should be possible to inactivate this putative protection mechanism by decreasing the RdRP activity. This inactivation could be performed, for example, by "antisensing" the RdRP mRNA, or by ribozymes, molecules which combine antisense and ribozyme functions, molecules which provide for cosuppression effects, or by tagging the plant RdRP gene. For both purposes the knowledge of the RdRP cDNA or RdRP gene sequence is a prerequisite. In order to post-transcriptionally silence the RdRP gene, real "antisense" transgene constructs have to be designed. It is easy to understand that a "sense" transgene construct does not make sense because the enzyme that is to be inactivated is just exactly the enzyme that can synthesize "antisense" RNA from "sense" RNA templates. The "antisense approach" to decrease the RdRP protein concentration could have the advantage of not completely destroying RdRP activity. In case the RdRP bears an essential part in healthy plants, the total loss of RdRP would be a lethal factor. As a function of the promoter driving a transgenic "antisense" construct or as a function of the transgene integration locus, plants could be isolated that show lower RdRP levels than wild-type plants. To analyse whether plants are able to survive without any RdRP activity, the RdRP gene can be knocked-out by gene tagging experiments. Foreign DNAs, as for example the T-DNAs of *Agrobacterium tumefaciens*, integrate into the plant genome at random loci. Provided that the sequence of the RdRP gene is known, plants can be screened for T-DNA insertions at the RdRP gene locus by PCR (Koes et al., 1992). Plants in which successful tagging of the RdRP gene occurred, should survive because in a diploid plant only one allele is inactivated. In case RdRP-minus plants show normal growth, progeny homozygous for the insertion allele are obtained after selfing.

When using the antisense approach for reduction of the above described enzymatic activity in plant cells, the nucleic acid molecule encoding the antisense-RNA is preferably of homologous origin with respect to the plant species used for transformation. However, it is also possible to use heterologous nucleic acid molecules which display a high degree of homology to endogenously occurring nucleic acid molecules encoding a polypeptide with the respective enzymatic activity. In this case the homology is preferably higher than 80%, particularly higher than 90% and still more preferably higher than 95%.

For the expression of the nucleic acid molecules according to the invention in sense or antisense orientation in plant cells, the molecules are placed under the control of regulatory elements which ensure the expression in plant cells. These regulatory elements may be heterologous or homologous with respect to the nucleic acid molecule to be expressed as well with respect to the plant species to be transformed. In general, such regulatory elements comprise a promoter active in plant cells. To obtain expression in all tissues of a transgenic plant, preferably constitutive promoters are used, such as the 35 S promoter of CaMV (Odell et al., Nature 313 (1985), 810–812) or promoters of the polyubiquitin genes of maize (Christensen at al., Plant Mol. Biol. 18 (1982), 675–689). In order to achieve expression in specific tissues of a transgenic plant it is possible to use tissue specific promoters (see, e.g., Stockhaus et al., EMBO J. 8 (1989), 2245–2251). Known are also promoters which are specifically active in tubers of potatoes or in seeds of different plants species, such as maize, Vicia, wheat, barley etc. inducible promoters may be used in order to be able to exactly control expression. An example for inducible promoters are the promoters of genes encoding heat shock proteins.

The regulatory elements may further comprise transcriptional and/or translational enhancers functional in plants cells.

Furthermore, the regulatory elements may include transcription termination signals, such as a poly-A signal, which lead to the addition of a poly A tail to the transcript which may improve its stability.

In the case that a nucleic acid molecule according to the invention is expressed in sense orientation it is in principle possible to modify the coding sequence in such a way that the polypeptide is located in any desired compartment of the plant cell. These include the endoplasmatic reticulum, the vacuole, the mitochondria, the plastides, the apoplast, the cytoplasm etc. Methods how to carry out these modifications and signal sequences ensuring localization in a desired compartment are well known to the person skilled in the art.

Methods for the introduction of foreign DNA into plants are also well known in the art. These include, for example, the transformation of plant cells or tissues with T-DNA using *Agrobacterium tumefaciens* or *Agrobacterium rhizogenes* (EP-A 120 516; EP-A 116 718; Hoekema in: The Binary Plant Vector System, Offsetdrukkerij Kanters BV, Alblasserdam (1985), Chapter V; Fraley et al., Crit. Rev. Plant Sci. 4, 1–46 und An et al., EMBO J. 4 (1985), 277–287), the fusion of protoplasts, direct gene transfer (see, e.g., EP-A 164 575), injection, electroporation, biolistic methods like particle bombardment and other methods known in the art.

The transformation of most dicotyledonous plants is possible with the methods described above. But also for the transformation of monocotyledonous plants several successful transformation techniques have been developed. These include the transformation using biolostic methods (Wan and Lemaux, Plant Physiol. 104 (1994), 37–48; Vasil et al., Bio/Technology 11 (1993), 1553–1558), protoplast transformation, electroporation of partially permeabilized cells, introduction of DNA using glass fibers, etc.

The reduction of the synthesis of a polypeptide according to the invention in the transgenic plant cells results in an alteration in the modulation of gene expression. In transgenic plants comprising such cells this can lead to various physiological, developmental and/or morphological changes.

The present invention also relates to transgenic plants comprising the above-described transgenic plant cells.

The present invention also relates to cultured plant tissues comprising transgenic plant cells as described above which either show overexpression of a polypeptide according to the invention or a reduction in synthesis of such a polypeptide.

In yet another aspect the invention also relates to harvestable parts and to propagation material of the transgenic plants according to the invention which either contain transgenic plant cells producing a polypeptide according to the invention (and if an endogenous RdRP gene is present in the plant above the wild type level of RdRP in said plant) or which contain cells which show a reduced activity of the described polypeptide. Harvestable parts can be in principle any useful parts of a plant, for example, leaves, stems, fruit, seeds, roots etc.

Propagation material includes, for example, seeds, fruits, cuttings, seedlings, tubers, rootstocks etc.

In general, the plants which can be modified according to the invention and which either show overexpression of a polypeptide according to the invention or a reduction of the synthesis of such a polypeptide can be derived from any desired plant species. They can be monocotyledonous plants or dicotyledonous plants, preferably they belong to plant species of interest in agriculture, wood culture or horticulture interest, such as crop plants (e.g. maize, rice, barley, wheat, rye, oats etc.), potatoes, oil producing plants (e.g. oilseed rape, sunflower, pea nut, soy bean, etc.), cotton, sugar beet, sugar cane, leguminous plants (e.g. beans, peas etc.), wood producing plants, preferably trees, etc.

It is furthermore possible to use the nucleic acid molecules, vectors and/or polypeptides of the invention and, optionally, an appropriate RdRP template nucleic acid molecule which may be identified by the afore-described method for inhibiting expression of any desired gene by transferring the RdRP system to organisms that either lack a comparable mechanism or do not sufficiently express their own RdRP. Furthermore, the nucleic acid molecules, vectors, antibodies and/or antagonist/inhibitors of the present invention can be used for inhibiting RNA-directed RNA synthesis and thereby conferring stable heterologous gene expression in transgenic organisms.

Besides the above-described possibilities to use the nucleic acid molecules, vectors and polypeptides according to the invention for e.g. the genetic engineering of organisms and their use to identify homologous molecules, the described nucleic acid molecules may also be used for several other applications, for example, for the identification of nucleic acid molecules which encode polypeptides which interact with the RdRP described above. This can be achieved by assays well known in the art, for example, by use of the so-called yeast "two-hybrid system". In this system the polypeptide encoded by the nucleic acid molecules according to the invention or a smaller part thereof is linked to the DNA-binding domain of the GAL4 transcription factor. A yeast strain expressing this fusion protein and comprising a lacZ reporter gene driven by an appropriate promoter, which is recognized by the GAL4 transcription factor, is transformed with a library of cDNAs which will express plant proteins fused to an activation domain. Thus, if a polypeptide encoded by one of the cDNAs is able to interact with the fusion protein comprising at least part of the RdRP polypeptide complex is able to direct expression of the reporter gene. In this way the nucleic acid molecules according to the invention and the encoded RdRP can be used to identify proteins interacting with the RdRP, such as protein kinases, transcription factors and the like. Other methods for identifying proteins which interact with the proteins according to the invention or nucleic acid molecules encoding such molecules are, for example, the in vitro screening with the phage display system as well as filter binding assays.

Figure 1:
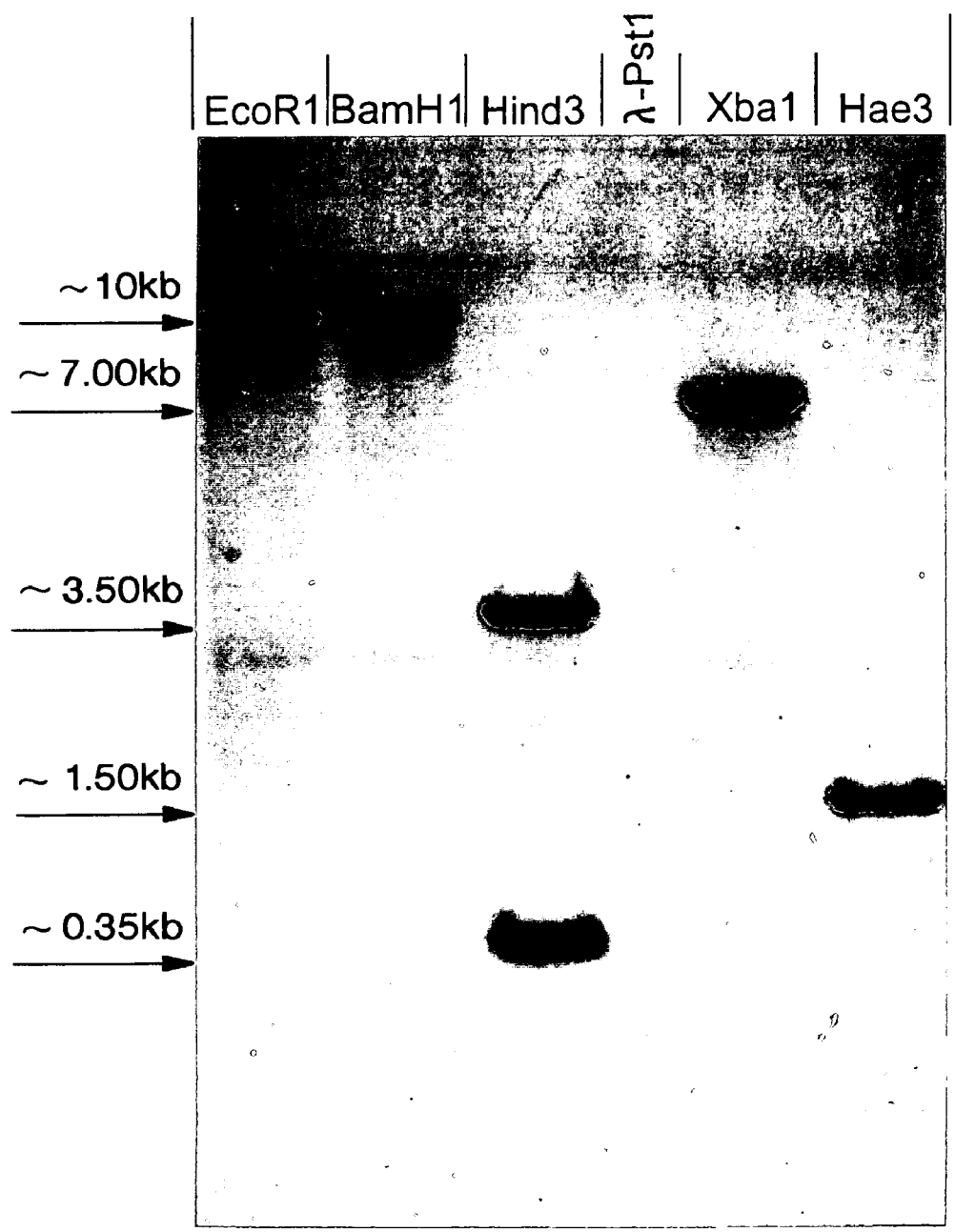
FIG. 1

15 µg of genomic tomato DNA (cv. Rentita) were cut with EcoR1 (lane 1), BamH1 (lane 2), Hind3 (lane 3), Xba1 (lane 5), and Hae3 (lane 6), respectively, (5U/µg) and electrophorized in a 13×18 cm 0.8% TEA-agarosegel. The DNA was then vacuum-blotted onto a nylon membrane and hybridized against a radom primed $^{32}$P-labeled RdRP-specific cDNA fragment as a probe.

The membrane was autoradiographed for 16 h at −80° C. using a BIOMAX™ MR film (Kodak) and a QuantalII-intensifying screen (Du Pont).

Lane 4: molecular weight standard, λDNA cut with Pst 1.

FIG. 2

15 µg of genomic DNA isolated from potato (lane 1), tobacco (lane 2), and the two tomato cultivars "St. Pierre" (lane 4) and "Retinta" (lane 5) were cut with Hind3 (5U/µg) and electrophorized in a 13×18 cm 0.8% TEA-agarosegel. The DNA was then vacuum-blotted onto a nylon membrane and hybridized against a radom primed $^{32}$P-labeled RdRP-specific cDNA fragment as a probe.

The membrane was at first autoradiographed for 16 h to visualize lane 1, 4, and 5 and then for 72 h to visualize lane 2 at −80° C. using a BIOMAX™ MR film (Kodak) and a QuantalII-intensifying screen (Du Pont).

Lane 4: molecular weight standard, λ-DNA cut with Pst 1.

FIG. 3

15 µg of total RNA isolated from PSTVd-infected (+) and viroid-free (−) tomato plants (cv. Rutgers and cv. Basket Pak, respectively), were denaturated by glyoxalation and electrophorized in a 13×18 cm 1.5% phosphate-buffered agarosegel. The RNA was then capillar-blotted onto a nylon membrane and hybridized against a radom primed $^{32}$P-labeled RdRP-specific cDNA fragment as a probe.

The membrane was autoradiographed for 16 h at −80° C. using a BIOMAX™ MR film (Kodak) and a QuantalII-intensifying screen (Du Pont).

FIG. 4

1 µl aliquods of elution fractions from 4 different protein purification columns (lane 2 and 3: Q Sepharose FF, lane 4: Poly(A) Sepharose, lane 5: Poly(U) Sepharose, and lane 6: Heparin Sepharose) that contained the highest RdRP activity were applied onto SDS-PAGE (Phast system, Pharmacia) and were then subjected to Western analysis. Immuno-detection was performed with the RdRP-specific antibody $A_{P431}$.

Lane M: molecular weight protein standard (205, 116, 97, and 58 kDa proteins).

Lane 1: 1 µl aliquod of the protein extract that was subsequently loaded onto the Q Sepharose FF column.

Numbers in parentheses are corresponding to the numbers of two Q Sepharose FF elution fractions.

FIG. 5

1 µl aliquods of the Sephadex G-200 gel filtration fractions [lane 2: retention volume fraction (rvf) 12, lane 3: rvf 14, lane 4: rvf 15, lane 5: rvf 17, and lane 6: rvf 19] were applied onto SDS-PAGE (Phast system, Pharmacia) and were then subjected to Western analysis. Immuno-detection was performed with the RdRP-specific antibody $A_{P431}$.

Lane 1: 1 µl aliquod of the protein extract that was subjected onto the column (ON).

FIG. 6

Design of RdRP-specific PCR-Primers.

EXAMPLES

Example 1

RdRP Purification

The concentration of plant-encoded RdRP in non-infected and apparently healthy plants is rather low. From 1 kg of apical tomato leaves corresponding to about 1000 tomato plants only about 10 to 20 µg of a protein preparation having RdRP activity could be isolated (Schiebel et al., 1993a). This low concentration is also reflected by the fact that the RdRP preparation from tomato leaves had to be concentrated ~100,000-fold to obtain at least an electrophoretic homogeneous protein preparation (Schiebel et al., 1993a). Microsequencing of protein preparations purified according to the method of Schiebel et al. (1993a) gave no reliable sequence information.

Thus, a new purification method had to be applied which was performed as follows. RdRP was solubilized from freshly harvested apical leaves of tomato plants (*Lycopersicon esculentum*, cultivar 'Rentita'). The plants that were grown under semi-controlled greenhouse conditions (25° C., 15-h photoperiod) were systemically infected (Tabler and Sänger, 1985) with the PSTVd type strain (Gross et al. 1978) at the two leaf stage i.e. about 4 weeks after sowing (Tabler and Sänger, 1984). Only the young and still unexpanded leaves from the shoot tips (about 1 g per plant) were harvested three to four weeks after inoculation.

Portions of 100 g each were homogenized with 500 ml of buffer A (50 mM Tris-acetate, pH 7.4, 10 mM K-acetate, 1 mM EDTA, 10 mM 2-mercaptoethanol, 0.5 mM PMSF) in a Waring type blender (Braunmixer MX 32) for 2 minutes at position 3. The homogenate was strained through 135 μm nylon sieve cloth (Nytal, Schweizer Seidengazefabrik, CH-9425 Thal SG/Swiss) and the retentate was rehomogenized with 220 ml of buffer A. The combined filtrates from 200 g of leaf material were centrifuged at 1.000×g for 15 minutes (Beckman Rotor J6B). The supernatant was mixed with 0.3 volumes of glycerol 86% and the mixture centrifuged at 30.000×g for 1 h in a Beckman type 19 rotor. The supernatant containing the "soluble RdRP" (RdRP-s) and the majority of TNTase was used for ammoniumaulfate precipitation.

The 30.000×g pellet containing RdRP was resuspended in 100 ml of buffer B (50 mM Tris-acetate, pH 8.2, 50 mM K-acetate, 1 mM EDTA, 25% (v/v) glycerol (Ph.Eur.III), 10 mM 2-mercaptoethanol, 0.5 mM PMSF) using a Dounce homogenizer. The suspension was slowly stirred for 30 minutes and centrifuged for 50 min at 40,000 rpm (146.000× g) in a Beckman rotor 50.2 Ti. The supernatant represents extract E1. The pellet was reextracted twice with 0.5 ml/g buffer B resulting in extract E2. Extracts E1 and E2 containing the 'membrane-bound RdRP' (RdRP-b) were shockfrozen in solid $CO_2$ and stored at −70° C. for loading onto a DEAE-Sepharose column.

The 30.000×g supernatant was mixed with the same volume of 3.95 M ammonium sulfate solution. After stirring for one hour at 4° C., the suspension was centrifuged at 10,000×g for 30 min. The pellet was dissolved with 40 ml of buffer C (25 mM Tris-acetate, pH 8.2, 1 mM EDTA, 20% glycerol, 3 mM 2-mercaptoethanol), dialyzed over night against 1 liter of buffer C, cleared by centrifugation at 10,000×g for 30 min, shockfrozen in solid $CO_2$ and kept at −70° C. for chromatography.

Both, supernatant and extracts from the pellet were assayed for RdRP activity as follows: The assay for RdRP activity is based on the incorporation of radioactively labeled 5'-nucleoside monophosphates from the corresponding [alpha-32P]NTPs into transcription products of a given RNA template. This assay is not RdRP-specific because the ubiquitous terminal nucleotidyl transferases (TNTase) are able to terminally incorporate radioactive ribonucleotides into polymeric RNA products. Such TNTases are RNA uridylyl-transferase (Zabel et al., 1981) (EC 2.7.7.52), polyadenylyl-transferase (Edmonds, 1982) (EC.2.7.7.19) or other TNTases (Boege, 1982) which usually contaminate RdRP preparations. No specific direct assays are available, as yet, that allow the unambiguous discrimination between the true template-directed transcription by RdRP and the terminal addition of nucleotides to the designated template RNA by TNTases. Consequently, RdRP and contaminating TNTases had to be separated from each other before their individual activities can be quantitated.

One unit of enzyme activity is defined as the amount of enzyme which catalyzes the incorporation of 1 nmol 5'-uridine monophosphate into high molecular weight RNA within 30 min. If not stated otherwise the assay was performed in prelubricated 1.7-ml test tubes (Sorenson Bioscience, Inc. Multi™ Liqid Handling Products, Salt Lake City, Utah, USA) in a final volume of 25 μl containing 50 mM Tris-acetate (pH 7.8), 10 mM Mg-acetate, 2 mM dithloerythritol, 0.3 mM each of ATP, CTP, GTP, 0.02 mM [alpha-$^{32}$P]UTP (adjusted to 0.5 Ci/mMol), 1 μg TMV RNA, 0.01% Tween 20, and 2 or 5 μl of RNA polymerase preparation. Reactions were initiated by adding the enzyme. After 30 min of incubation at 37° C., the reaction tubes were transferred to ice. After mixing with 15 μl of 13 mM UTP, 10 μl of water was added as a wash solution and the tube contents were spotted on Whatman 3MM paper strips (2×10 cm) before performance of descending chromatography in 2 M Na-acetate, pH 5.2/ethanol=1/1. The radioactivity of the RNA products remaining at the origin of the chromatogram was determined by liquid scintillation counting (6 ml cocktail rotiazint eco plus, Roth) and used for the calculation of enzyme activity. Under the given conditions and 5 μl RdRP/ assay a concentration of one unit per milliliter corresponded to 4800 cpm (Schiebel et al., 1993b). This assay was used throughout the examples unless otherwise stated.

The supernatant contained about 5 U per 150 g of leaves whereas the corresponding pellet contained about 1.4 U of extractable RdRP.

All RdRP preparations were first chromatographed on DEAE-Sepharose which removed nucleic acids, most of the pigments and an inhibitor of RdRP activity.

The extracts containing RdRP-b from the membrane-rich pellet or the ammonium sulfate-fractionated 30,000×g supernatant were loaded onto a column of DEAE-Sepharose Fast Flow (FPLC system, Pharmacia; 5 cm×10 cm) with a flow rate of 6 to 15 cm/h (2–5 ml/min) using a peristaltic pump.

After eluting non-adsorbed material with about 70 ml of buffer C, a linear gradient of 0.0 to 0.7 M ammonium acetate in buffer C was applied with a flow rate of 3 to 12 cm/h (1 to 4 ml/min) depending on the pressure limit of about 0.5 MPa. The volume of the gradient was 500 ml up to 0.5 M salt and 100 ml for the higher salt concentrations. Fractions of 20 ml were collected and those fractions containing the main enzyme activity were pooled, shockfrozen and stored.

The enzyme preparation from the DEAE-Sepharose chromatography containing about 0.27 M ammonium acetate was diluted with one volume of buffer D (20 mM Tris-HCl pH 8.0, 0.5 mM EDTA, 1.5 mM DTE, and 0.012% Tween 20) and loaded onto 3 ml poly(U)Sepharose 4B (Pharmacia) in a 1×3.7 cm column (FPLC system, Pharmacia: C10/10) equilibrated with buffer D. A total volume of 120 ml was loaded with a flow rate of 1 ml/min. After elution of nonadsorbed proteins with buffer D a linear gradient of 30 ml from 0.0 to 1 M NaCl in buffer D was applied and fractions of 1.5 ml wore collected. Those fractions containing enzym activity were pooled, shockfrozen and stored.

In order to concentrate the RdRP containing eluate from the first poly(U)-Sepharose chromatography the corresponding fractions were diluted with two volumes of buffer D and loaded on 0.4 ml poly(U)-Sepharose 4B in a 0.5×1.9 cm column (SMART system, Pharmacia; HR 5/2) with a flow rate of about 0.1 ml/min using a peristaltic pump. After elution of non-adsorbed proteins with buffer D the column was installed into the Smart system. Elution was performed by sodium chloride increasing in a linear gradient up to 1.5 M. The flow rate during elution was 0.05 ml/min. Fractions of 0.1 ml were collected. Those fractions containing enzyme activity were analyzed by SDS PAGE and pooled resulting in the partially purified RdRP preparation.

Pools from several chromatographic runs were collected. The proteins exhibiting a RdRP activity of 20 U in 4 ml desorption buffer (about 1 M NaCl in buffer D) were concentrated and concomitantly freed from salt by deoxycholate trichloroacetic acid precipitation (Bensadoun and Weinstein, 1976) in prelubricated 1.7-ml test-tubes. Insulin (25 μg/ml) was used as coprecipitant, centrifugation was performed in a swinging bucket rotor at 11,000 rpm for 30 minutes. The resulting pellets were washed with ethanol at −20° C. and used for analytical SDS PAGE (Phast system, Pharmacia). The estimated amount of RdRP protein was about 5 μg.

Example 2

Microsequencing of the RdRP Proteins

The precipitated protein was prepared for SDS PAGE, applied onto a 7% polyacrylamid gel (Laemmli) and stained with coomassie Brillant Blue R250 (Sambrook et al., 1989). The 128 kDa band was excised and cleaved in the gel according to Eckerskorn and Lottspeich (1989) except that instead of trypsin, endoprotease LysC (Boehringer Mannheim) with an enzyme:protein ratio of 1:10 (w/w) was used. The peptides separated by reversed phase HPLC were sequenced using a 492A amino acid sequencer (Applied Biosystems) according to the manufacturers instructions.

Example 3

Isolation of the RdRP cDNA

Micro-sequencing of the RdRP protein resulted in only four definite AS-sequences from which the corresponding nucleic acid sequence could be deduced. In FIG. 6 the sequence of two of the four peptides and the sequence of four of the corresponding synthetic oligonucleotides that had been designed for PCR-experiments are presented.

In order to perform PCR with the RdRP-specific primers, cDNA had been synthesized from tomato mRNA. For mRNA isolation 20 g of young leaves were harvested from potato spindle tuber viroid- (PSTVd) infected "Rutgers" tomato plants that were grown in the greenhouse (see above). The plant material was immediately frozen in liquid nitrogen, and total RNA was isolated as described by Logemann et al. (1987). From 5 mg of total RNA, polyA+ RNA was isolated using the 'PolyATtract mRNA isolation System I' (Promega) following the manufacturers instructions. Subsequently 1 μg of the purified polyA+ RNA was subjected to the 'cDNA Synthesis Kit' (Boehringer Mannheim) and cDNA was synthesized according to the manufacturers instructions using an oligo $(dT)_{15}$ primer. The reaction was stopped by phenol-extraction and 1 μl of the sample was diluted 1:100 with TE-buffer.

PCR was performed with 1 μl of the diluted cDNA and using the primer-pair A (RdRP/8H1-RdRP/15R1; 0.1 nmol each) and B (RdRP/15H1-RdRP/8R1; 0.1 nmol each), respectively. Amplifications were assayed in a 100 μl reaction-mix containing 10 μl of 10×Assay Buffer (Eurogentec), 10 μl of dNTPs (2 nmol/μl), and 1 μl of EuroTaq polymerase (4U/μl) (Eurogentec). The samples were transferred to a 'Crocodile II Thermocycler' block (Appligene) and 30 cycles were started (1' 95° C., 1' 55° C., and 1' 72° C.). After separation on a 0.8% TBE-agarose gel (Sambrook et al., 1989), analysis of the PCR products revealed that a single DNA fragment of about 800 bp in size had been amplified with primer pair B. This fragment ($RdRP_{800}$) was eluted from the agrose gel (QlAquick Gel Extraction Kit, Qiagen) and cloned (Sambrook et al., 1989) into the T/A-type PCR cloning vector pTPCR (Wassenegger et al., 1994) which is similar to the plasmid pCR™II that is delivered with the cloning™ Kit (Invitrogen).

The sequence of the $RdRP_{800}$ was determined on an automatic sequencer (ALFexpress, Pharmacia Biotech) using the 'Cy5 AutoRead Sequencing Kit' (Pharmacia Biotech) and following the manufacturers sequencing procedure. The precise length of $RdRP_{800}$ was 833 bp comprising an ORF that corresponds to 277 amino acid residues (AS) given in SEQ ID NO:3 which correspond to amino acid 700 to amino acid 917 of the amino acid sequence of SEQ ID No:2.

Two custom ZAP EXPRESS™ EcoRI cDNA libraries (Stratagene) had been established from polyA+ RNA which had been isolated as described above from young leaves of the tomato cultivars 'Rutgers' and 'Basket Pak'. From five to 10 μg of the purified $polyA^+$-enriched RNA cDNA libraries were constructed (Stratagene). The size-fractionated oligo(dT)-primed cDNAs (>500 bp) were ligated via EcoRI adaptors into the Lambda ZAP bearing pBK-CMV phagemid vector. This system has an cloning capacity of 12 kb and allows in vivo excision of the cloned fragments. However, the "Rutgers"- and "Basket Pak"-specific cDNA libraries produced by Stratagene had a representative size of 1.800 bp and $3.5 \times 10^8$ primary plaques.

Both libraries were screened three times by plaque hybridization following the instruction manual of the Stratagene ZAP EXPRESS™ EcoRI Library with the $^{32}$P-labeled $RdRP_{800}$-DNA fragment using the 'Random Primed DNA Labeling Kit' (Boehringer Mannheim). Altogether 23 recombinant plasmid DNAs that had been detected with the radioactive probe were excised in vivo from the phages and finally introduced into the XLOLR™ E.coli strain according to the Stratagene ZAP EXPRESS™ EcoRI Library instruction manual. Characterization of the plasmid inserts revealed that none of them corresponded to the minimum size of 3.000 bp which could be expected from a 120 kDa protein. The largest hybridizing EcoRI cDNA fragment (RdRP24) was about 2.300 bp in length, and it contained the entire 3'-part of the RdRP. In order to obtain the missing 5'-region of the RdRP cDNA, the 'rapid amplification of 5'-cDNA ends' (RACE) was performed. This PCR technique allows the amplification of cDNA by using one appropriate gene specific reverse primer (GSP) for which the sequence information about the 5'-end is not required.

Oligo-dT-primed cDNA was synthesized as described (see above) using polyA+ RNA that has been isolated from PSTVd-infected tomato plants. According to the "Marathon™ cDNA Amplification Kit" (Clontech) a particular adaptor was ligated to both ends of the produced double-stranded cDNA. The subsequent PCR amplification was performed with a 1:100 dilution of the 'adaptored' cDNA (1 μl/reaction) using an oligonucleotide that was complementary to the adaptor sequence (adaptor primer, AP) as a forward primer. As reverse primers, the following three different GSPs (GSP400, GSP420, and GSP1200) complementary to the known RdRP24-specific cDNA sequence were designed:

GSP400: 5'-CAT AAC GAA TCT GGA AAG CAG ATG G-3' (SEQ ID NO:4)

GSP420: 5'-GAT GAA TCC GGA TCA ACA CCC ACA C-3' (SEQ ID NO:5)

GSP1200: 5'-GGG TGC TGG AGG ATA TTC CAT CGG C-3' (SEQ ID NO:6)

Thermal cycle parameters as dependent on the annealing temperature of the GSP were as follows:

Program 1 (Tm: 60–65° C.) used for GSP400 (Tm=57.9° C.) and GSP420 (Tm=62.1° C.):

94° C. for 1 min; 30 cycles: 94° C./30 sec, 60° C./30 sec, 68° C./4 min

Program 2 (Tm: 65–70° C.) used for GSP1200 (Tm=66° C.):

94° C. for 1 min; 30 cycles: 94° C./30 sec, 68° C./4 min

In case of the GSP400-specific RACE reaction, a major product of about 1.900 bp was amplified. In consideration of a 400 bp long overlap with RdRP24 this 1.900 bp fragment contained a RdRP-specific 5'-end sequence of about 1.500 bp. In contrast to the AP/GSP400-specific PCR product, agarose/EtBr gel analysis of the AP/GSP420-specific PCR products revealed that shorter DNA fragments had been amplified. Because GSP420 was complementary to the RdRP24 sequence at position +420, the appearance of PCR products that were smaller than 1.900 bp in size indicated that predominantly inappropriate cDNAs had been synthesized. The reactions performed with the AP/GSP1200 resulted in fragments of 2.700 bp in length. After substraction of 1.200 bp which are provided by the overlap between GSP1200 and RdRP24, the remaining fragment again indicated that the RdRP24 cDNA clone has to be extended by 1.500 bp to give a full-length RdRP-specific cDNA of about 3.800 bp in size.

Several inserts of different length were obtained after cloning of the gel-purified AP/GSP400-specific PCR products into pTPCR (see above). Sequence analysis (see above) of the largest RACE clones had shown that the cloned insert most likely comprised the complete 5'-end of the RdRP-specific cDNA. Computer-supported sequence analysis (DNASIS, Pharmacia) of a fusion of the AP/GSP400-specific RACE product with the RdRP24 sequence revealed the entire RdRP cDNA sequence (SEQ ID NO:1) with an Open Reading Frame of 1114 amino acids and a calculated molecular weight of the RdRP protein of about 127 kDa which is in good agreement with the experimental values that had been determined by SDS-PAGE (128 kD) and sucrose gradient centrifugation (119 kD) (Schiebel et al., 1993a).

In order to physically generate of a full-length cDNA clone, many efforts were made to connect the RdRP24 fragment with the AP/GSP400-specific PCR product. Although a suitable unique Aspl restriction site was found to be present in the overlapping aera of both subclones, cloning of the gel purified DNA fragments into different vectors and transformation into different *E. coli* strains failed. Because none of these attempts was successful, the PCR technique was again utilized to produce the entire RdRP cDNA.

For this purpose forward primers had been designed that were specific to region 30 (P127BamA) and to region 140 (P127BamB) of the 5'-nontranslated region of the RdRP sequence (see above). As a reverse primer, an oligonucleotide (P127Bgl) complementary to the 3'-nontranslated region (position 3630, see above) was synthesized.

P127Bam1: 5'-CTT CAC CAG GGA TCC ACT CAT CAC TCC CCT CAA G-3' (SEQ ID NO:7)

P127Bam2: 5'-GCA TAA CTT CAG GGG GGA TCC AGT TGG TGT TAG C-3' (SEQ ID NO:8)

P127BGL: 5'-GCA GCT TCA TGC AGA TCT AAA GAC AAA AGG TAG TC-3' (SEQ ID NO:9)

To enhance the cloning efficiency these oligonucleotides contained a unique restriction site, i. e. a BamHI sites in case of the forward primers, and a BglII site in case of the reverse primer. PCRs were performed with tomato cDNA as descibed above, running the thermo cycler program 1 and using P127Bgl (Tm=65.6° C.) in combination with either P127BamA (Tm=72.5° C.) or with P127BamB (Tm=71.1° C.). As a result, major products of the expected sizes ranging between 3.500 and 3.600 bp were obtained. After double digestion with BamHI/BglII the PCR products were cloned into the plasmid vector pT3T7 (Boehringer Mannheim) that had been previously cut with BamHI. Sequence analysis of four independent clones revealed that all RdRP-specific inserts represented the entire RdRP cDNA. Unfortunately it turned out that they all contained several substitutions when compared with each other, and also when compared with the original chimeric sequence. Although most of these mutations were found to be "still", because only the third position of a codon triplett was affected, others could lead to an unwanted translational stop. The error rate of the EuroTaq polymerase (Eurogentec) is obviously too high to amplify 3.500 bp fragments without nucleotide substitutions. Therefore, another PCR approach was performed under reaction conditions as described above but using the Expand™ High Fidelity PCR System (Boehringer Mannheim). This system utilizes a mixture of the Taq and the Pwo DNA polymerase, the later enzyme possesses an efficient 3'–5' proofreading ability. RdRP-specific products were again amplified, and after sequencing of the corresponding cloned cDNAs it was demonstrated that a lower error rate had occurred within the sequences. Finally, one clone (RdRP/HF) only contained two "still" nucleotide substitutions. The mutations within the RdRP/HF sequence are presented in FIG. 3/1. The RdRP/HF 5'-BamHI site, and the BglII site which is located at the 3'-end of RdRP and which is destroyed upon cloning a BglII fragment into a BamHI site are also shown.

TABLE 1

```
           BamHI                                         (BglII/BamHI)
           :        10           1995            2235           :3375
           :   *         *    *          *    *          *:   *
RdRP/HF    GGATCCACTC-//-GATTACTCTC-//-CGACTTGCGG-//-ATAAGAGATC C
              30|             |2020        |  2260          3600 |
              *|   *         * |  *        |*    *         *  | |* |
RdRP cDNA  GGATTGACTC-//-GATTACGCTC-//-CGATTTGCGG-//-ATAAGAAAAC T
```

Table 1: Partial alignment of the RdRP/HF and the RdRP cDNA sequences The nucleotide substitutions detected within the coding region of the RdRP/HF sequence are underlined. Letters set in italics are indicating the cloning sites.

Example 4

Southern Analysis of Tomato Genomic DNA

Tomato genomic DNA was analysed to determine the copy number and the genome organization of the RdRP gene. The knowledge of the RdRP cDNA sequence and the computer-supported compilation (DNASIS, Pharmacia) of its restriction map allows the detection of gene-exons and gene-introns by Southern hybridization of genomic DNA.

Genomic DNA was extracted from tomato leaves (20 g) according to the procedure of Bedbrook (1981). 15 μg of purified DNA were cut with EcoRI, BamHI, HindIII, XbaI, and HaeIII (all enzymes from Boehringer Mannheim), respectively, and electrophorized on a 0.8% TAE agarose gel (Sambrook et al. 1989). After the denaturation and renaturation of the agarose gel, the DNA was transferred (Vacuum Blotter, Appligene) to positively charged Nylon Plus membrane (Qiagen), and finally UV$_{312nm}$ crosslinked (0.3J/cm$^2$). Hybridization of the Southern blot agains random primed $^{32}$P-labeled RdRP24 DNA (see above) was performed as described by Amasino (1986). Briefly, blots were hybridized at 42° C. in 0.25 M NaHPO$_4$, pH 7.2, 0.25 M NaCl, 7% SDS, 1 mM EDTA, 50% formamide with or without 5–20% (w/v) PEG (M$_r$ 6–7.5×10$^3$) or DexSO$_4$ (M$_r$ 5×10$^5$) on a rocker platform. Prehybridization was for 5–10 minutes without change of solution. After hybridization, blots were washed once in 2×SSC (1×SSC=0.15M NaCl, 0.015 M Na Citrate, pH 7.0) for five minutes at room temperature, twice in 0.25 M NaHPO$_4$, 2% SDS, 1 mM EDTA for 20–60 minutes at 65° C.

The autoradiograph of the Southern blot (exposed for 16 hours) is shown in FIG. 1. The endonucleases EcoRI and BamHI do not cut within the RdRP cDNA and most likely there is also no restriction site within the RdRP gene. Therefore the single band of about 10.000 bp (lane 1 and lane 2), respectively, indicates that the RdRP gene exists as a single copy gene within tomato genome. This assumption is supported by the occurrence of only a single hybridizing fragment in lane 4. Because XbaI cuts only once within the RdRP cDNA, the second XbaI site must be located in the flanking genomic DNA close to the RdRP gene sequence. As a consequence, if the plant contains two independent RdRP genes two fragments should be released by XbaI.

The banding pattern of the hybridizing HindIII fragments clearly demonstrates that the RdRP gene is composed of exons and introns. The size of the HindIII fragments that can be deduced from the restriction map of RdRP cDNA sequence should result in a 130 bp fragment and two border fragments with sizes larger than 600 bp. The appearance of a 350 bp fragment (lane 3) can only be explained by an additional HindIII site that is located within an intron sequence.

A similar situation is given when the HaeIII digest is analysed. The expected size of a HaeIII-specific fragment is about 990 bp. However, there is no signal visible on the autoradiograph that corresponds to this size range (lane 6). The larger hybridizing fragment of 1.500 bp in size must be due to an intron within the 990 bp cDNA fragment.

A more detailed analysis of the tomato RdRP gene by characterization of clones that had been isolated from two custom ZAP EXPRESS™ EcoRI cDNA genomic libraries (Stratagene) is in progress. So far, the entire sequence of the coding region could be confirmed, and the existence of at least three introns could also be demonstrated (data not shown).

Example 5

Southern Analysis of Different Plant Genomic DNAs

Figure 2:

Of particular interest is the examination of the distribution of the RdRP gene over different plant species. Therefore Southern hybridization was performed as described above, but now HindIII-restricted genomic DNA of the two different tomato cultivars 'Rutgers' and 'St. Pierre', as well as nuclear DNA of potato and tobacco was analysed. The autoradiograph of the Southern blot (exposed for 16 h lane 1,3, and 4; exposed for 72 h lane 2) revealed that the RdRP gene is detectable in all four genomes (FIG. 2). The strong cross-hybridization of the potato DNA with the tomato-specific probe (lane 1) is not unexpected because potato is a plant that is closely related to tomato. The weak 'tobacco signals' (lane 2) might be due to the fact that tobacco is more distantly related to tomato. In addition, the tobacco genome is much more complex than that of tomato and potato, respectively. In case the same amounts of genomic DNA are loaded on the agarose gel, the number of a particular DNA sequence, for example that of the RdRP gene, is less well represented when the genome is more complex.

Nevertheless, the existence of a tobacco RdRP gene was also demonstrated by the characterization of a 850 bp long PCR product that had been amplified with genomic tobacco DNA and using tomato RdRP cDNA-specific primers (data not shown).

Example 6

Northern Analysis of Total Tomato RNA

Total RNA was isolated as described above from PSTVd-infected and from viroid-free tomato plants (cv. 'Rutgers' and cv. 'Basket Pak'). Separation of total RNAs (15 μg/lane) was performed in phosphate-buffered 1.5% agarose gels. The RNAs were pretreated with 1 vol. DMSO-mix in a final volume of 50 μl and heat-denaturated at 65° C. for 10 min. (Splesmacher et al., 1985). The RNAs were transferred onto non-charged nylon membranes (Qiabrane, Qiagen) by capillar blotting as described by Sambrook et al. (1989) and hybridized against radom primed $^{32}$P-labeled RdRP24 DNA (see above).

Figure 3:
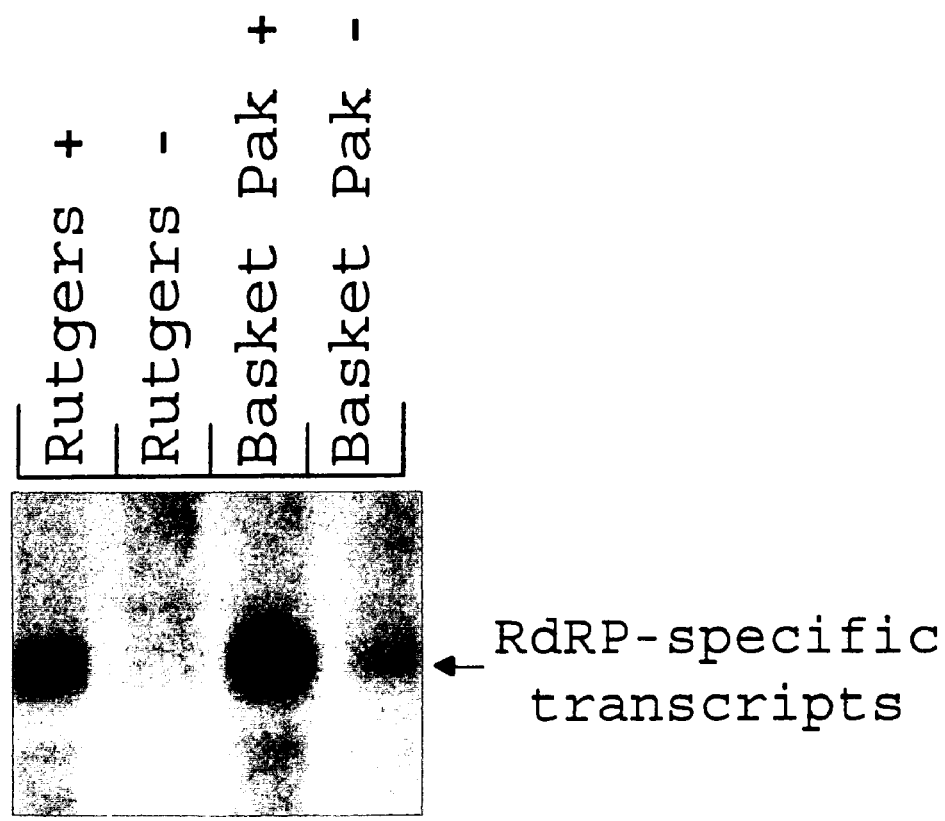

The autoradiograph of the Northern analysis which was exposed for 16 h shows that the RdRP gene is transcribed, and moreover it shows that transcription is induced upon PSTVd-infection (FIG. 3, compare lane 1 and 3 with lane 2 and 4). This result is in good agreement with the observation that the amount of RdRP protein is also increased in viroid infected tomato plants.

Example 7

Verification of the RdRP cDNA Encoded Protein

In order to examine whether the RdRP cDNA encoded protein (C-protein) is identical with the isolated enzyme, four different C-protein-specific antibodies had been produced (Eurogentec). From the entire AS sequence of the C-protein the following peptides had been synthesized and were chosen for immunisation of rabbits (Eurogentec):

P430: SNRVLRNYSEDIDN (SEQ ID NO:10)
P431: ASKTFDRRKDAEAI (SEQ ID NO:11)
P432: EQYDGYLKGRQPPKSPS (SEQ ID NO:12)
P433: VFPQKGKRPHNEC (SEQ ID NO:13)

The specific reaction of each antiserum with the RdRP protein isolated from the tomato leaf tissue was tested by Western blotting (Sambrook et al., 1989). The four antisera were able to immunologically detect a protein at the position of the RdRP activity (data not shown). Subsequently the two most sensitive antisera were applied onto a peptide/antigen matrix column for affinity purification (Eurogentec). The purified P431 antiserum (A$_{P431}$) was used in all experiments described below.

Figure 4:
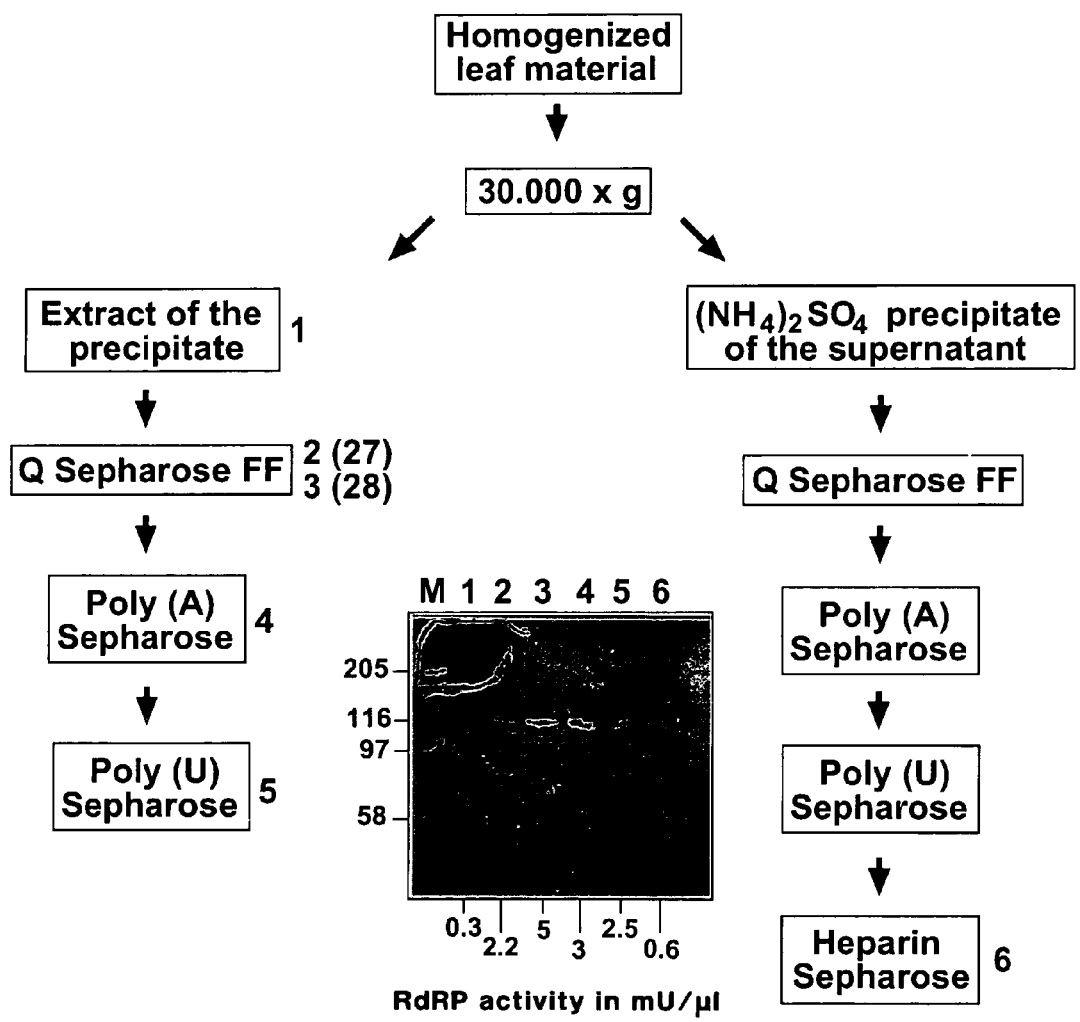

Specific immunological detection of the active RdRP protein with A$_{P431}$ was analysed with elution fractions from four different chromatographic runs. 1 μl aliqiods of those fractions that contained the highest RdRP activity were applied onto SDS-PAGE (Phast system, Pharmacia) and were then subjected to Western analysis (FIG. 4). As shown in FIG. 4 the intensity of the A$_{P431}$-specific signal correlates with the enzyme activity in that only those fractions reacted with A$_{P431}$ that also contained active RdRP. As a control the protein sample that was run in lane 1 originates from the resuspended '30.000×g precipitate' (see above) that was loaded on the Q Sepharose FF column. The additional signal that is visible in lane 2 and 3 was demonstrated to be due to reaction of a pre-serum-specific antibody with a protein that is eluted from the Q-Sepharose FF column together with the RdRP protein.

Figure 5:
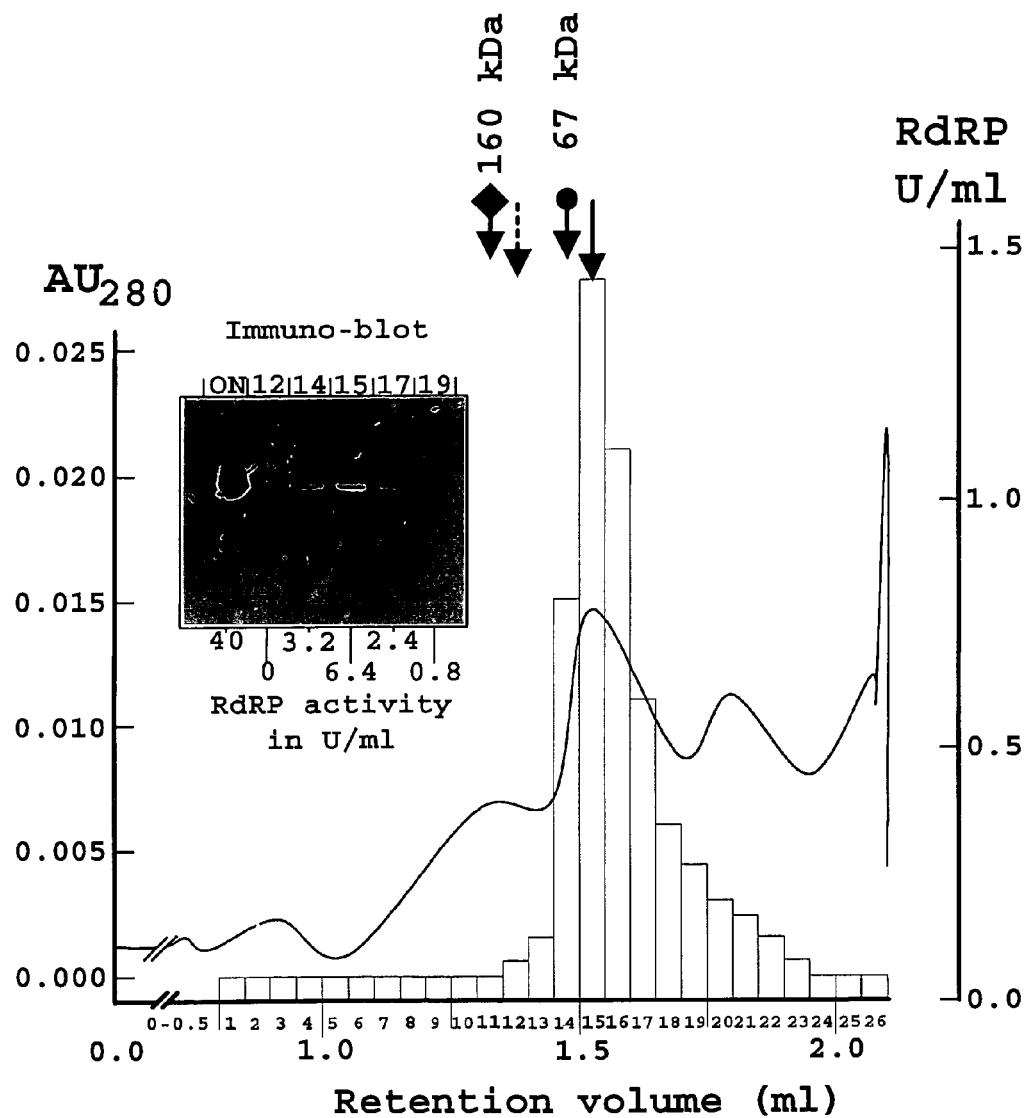

Additional evidence of the averment that the RdRP cDNA encodes the RdRP enzyme came from a gel filtration experiment (FIG. 5). The Sephadex G-200 gel system is used to separated proteins according to their molecular weight. This size fractionation procedure was originally conceived to further purify the plant RdRP protein. Surprisingly enough the retention volume for the elution of the tomato enzyme corresponded to a protein with a size of less than 65 kDa. As shown in FIG. 4 the highest RdRP activity was found in fraction 15 and not in fraction 13 as expected. But with the aid of SDS-PAGE analysis it was demonstrated that fraction 15 contained a 128 kDa protein and moreover this protein was detected by $A_{P431}$ (FIG. 4., Immuno-blot, lane 15).

The present invention is not to be limited in scope by the specific embodiments described which are intended as single illustrations of individual aspects of the invention, and any nucleic acid molecules, proteins, constructs or antibodies which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

REFERENCES

Amasino R. M. (1986). Acceleration of nucleic acid hybridization rate by polyethylene glycol.
Anal. Biochem. 152: 304–307
Bedbrook J. (1981). A plant nuclear DNA preparation procedure.
Plant Mol. Biol. News 2: 24
Bensadoun A. and Weinstein D. (1976). Assay of proteins in the presence of interfering materials.
Anal. Blochem. 70, 241–250
Boege F. (1982). Simultaneous presence of terminal adenylyl, cytidylyl, guanylyl, and uridylyl transferase in healthy tomato leaf tissue: Separation from RNA-dependent RNA polymerase and characterization of the terminal transferases.
Biosci. Rep. 2, 379–389
Dorssers L., van der Meer J., van Kammen A., and Zabel P. (1983). The Cowpea Mosaic Virus RNA replication complex and thaw host-encoded RNA-dependent RNA Polymerase-template complex are functionally different.
Virology 125, 155–174
Eckerskorn C. and Lottspelch F. (1989). Internal amino acid sequence analysis of proteins separated by gel electrophoresis after tryptic digestion in polyacryamide matrix.
Chromatographia 28: 92–94
Edmonds M. (1982). Poly(A) adding enzymes.
In The Enzymes,. 3rd Ed., 15: 218–250
Fraenkel-Conrat H. (1986). RNA-dependent RNA Polymerases
Critical Reviews In Plant Science 4: 213–226
Gross H. J., Domdey H., Lossow C., Jank P., Raba M., Alberty H., and Sanger H. L. (1978). Nucleotide sequence and secondary structure of potato spindle tuber virold.
Nature 273: 203–208
Koes R., Souer E., van Houwelingen A., Mur L., Spelt C., Quattrocchio F., Wing J.,Oppedijk B., Ahmed S., Maes T., Gerats T., Hoogeveen P., Meesters M., Kloos D., and Mol J. N. M. (1995). Targeted gene inactivation in petunia by PCR-based selection of transposon insertion mutants.
Proc. Nati. Aced. Sci. USA 92: 8149–8153.
Khan Z. A., Hiriyanna K. T., Chavez F., and Fraenkel-Conrat H. (1986). RNA-directed RNA polymerase from healthy and from virus-induced Cucumber.
Proc. Nati. Acad. Sci. USA 83, 2383–2386
Logemann J., Schell J., and Willmitzer L. (1987). Improved method for the isolation of RNA from plant tissues.
Anal. Biochem. 163: 16–20
Meyer P. (1996). Homology-dependent gene silencing in plants. Ann. Rev. Plant Physiol. Plant Mol. Biol. 47: 23–48
Sambrook J., Fritsch E. F., and Maniatis T. (1989). Molecular cloning: A laboratory Manual,
Second edition (Cold Spring Harbor, N.Y.: Cold Spring Harbor Laboratory Press).
Schiebel W., Haas B., Marinkovic S., Klanner A., and Sänger H. L. (1993a). RNA-directed RNA polymerase from tomato leaves I. Purification and physical properties.
J. Biol. Chem. 268: 11851–11857
Schiebel W., Haas B., Marinkovic S., Klanner A., and Sänger H. L. (1993b). RNA-directed RNA polymerase from tomato leaves II. Catalytic in vitro properties.
J. Biol. Chem. 268: 11858–11867
Splesmacher E., Muehlbach H. P., Tabler M., and Sänger H. L. (1985). Oligomeric forms of potato spindle tuber vimid (PSTV) and its complementary RNA are present in nuclei isolated from virold-infected potato cells.
Biosc. Rep. 5: 251–265
Tabler M. and Sänger H. L. (1984). Infectifity studies on different potato spindle tuber viroid (PSTV) RNAs synthesized in vitro with the SP6 transcription system.
EMBO J. 3: 3055–3062
Wassenegger M., Heimes S., Sänger H. L. (1994). An infectious viroid RNA replicon evolved from an in vitro-generated non-infectious viroid deletion mutant via a complementary deletion in vivo.
EMBO J. 13: 6172–6177
Weissbach A. and Poonian M. (1974). DNA Cellulose Chromatography Methods Enzymol. 34: 463–475
Zabel P., Dorssers L., Wemars K., and van Kammen A. (1981). Terminal uridylyl transferase of Vigna unguiculata: Purification and characterization of an enzyme catalyzing the addition of a single UMP residue to the 3'-end of an RNA primer.
Nucleic Acids Res. 9: 2433–245

We claim:

1. An isolated transgenic plant cell comprising a foreign nucleic acid molecule stably integrated into the genome, wherein the nucleic acid molecule is a nucleic acid molecule encoding a polypeptide having the enzymatic activity of an RNA-directed RNA polymerase (RdRP), selected from the group consisting of:

(1) a nucleic acid molecule coding for a polypeptide comprising the amino acid sequence of SEQ ID NO: 2;
   (2) a nucleic acid molecule comprising the coding region of the nucleotide sequence of SEQ ID NO: 1; and
   (3) a nucleic acid molecule that specifically hybridizes to a complementary strand of the nucleic acid molecule as defined in (1) or (2) in 0.25 M $NaHPO_4$ pH 7.2; 0.25 M NaCl, 7% SDS, 1 mM EDTA, 50% formamide and 5–20% (w/v) polyethylene glycol ($M_r$ 6–7.5×10$^3$) at 42° C. for 4–24 hours followed by washing once in 2×SSC at room temperature, and twice in 0.25 M $NaHPO_4$, 2% SDS, 1 mM EDTA at 65° C., said specifically hybridizing nucleic acid being more than 90% identical to the coding region of SEQ ID NO: 1;

wherein said nucleic acid molecule is linked to regulatory elements such that the nucleic acid is expressed in plant cells.

2. The transgenic plant cell according to claim 1, wherein the nucleic acid molecule is DNA.

3. The transgenic plant cell according to claim 2, wherein the DNA is cDNA or genomic DNA.

4. The transgenic plant cell according to claim 1, wherein the nucleic acid molecule is RNA.

5. The transgenic plant cell according to claim 1, wherein the nucleic acid molecule is derived from a plant cell.

6. The transgenic plant cell according to claim 5, wherein the nucleic acid molecule is derived from a tomato plant cell.

7. The transgenic plant cell according to claim 1, wherein the nucleic acid molecule is selected from the group consisting of the nucleic acid molecule encoding the amino acid sequence of SEQ ID NO:2 and the nucleic acid molecule comprising the coding region of the nucleotide sequence of SEQ ID NO: 1.

8. A transgenic plant comprising the plant cell of any one of claims 1 or 2–7.

9. The isolated transgenic plant cell of claim 1 wherein said nucleic acid is stably integrated into the genome of said plant cell and expression of the nucleic acid molecule leads to reduction of the synthesis of a polypeptide having RNA-directed RNA polymerase (RdRP) activity in the cell.

10. The transgenic plant cell of claim 9, wherein the reduction is achieved by an antisense or co-suppression effect.

11. A transgenic plant comprising the plant cell according to claim 9 or 10.

12. A cultured plant tissue comprising the plant cell according to any one of claims 1, 9 or 10.

13. A leaf, stem, fruit, seed, or root of a plant, wherein said leaf, stem, fruit, seed, or root comprises the plant cell according to any one of claims 1, 9 or 10.

14. Propagation material of a plant, wherein said propagation material comprises the plant cell according to any one of claims 1, 9 or 10.

15. The transgenic plant cell according to claim 1, wherein said nucleic acid molecule is heterologous to the transgenic plant cell.

* * * * *

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
      (A) LENGTH: 3731 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (A) ORGANISM: Tomato (ix) FEATURE:
      (A) NAME/KEY: CDS
      (B) LOCATION: 194..3535

(xi) SEQUENCE DESCRIPTION: SEQ ID NO: 1:

```
GAAATATTCT TTACTTACTT CACCAGGGAT TGACTCATCA CTCCCCTCAA GTCTTTGTGT        60

GTTGTGATAA TAAATTTGGT TGTGCTTCAG TTTCAGTCAC TACTGCTGGG TAGTTTTTAT       120

TTTGCATAAC TTCAGGGGGT ATTCCAGTTG GTGTTAGCAT TTGAAAGTCG AACTGCACTT       180

GGAATTTGGC TAC ATG GGA AAG ACA ATT CAG GTT TTC GGA TTC CCT TAT         229
            Met Gly Lys Thr Ile Gln Val Phe Gly Phe Pro Tyr
              1               5                  10

CTT CTC TCT GCG GAA GTG GTT AAG TCA TTC TTA GAG AAA TAT ACA GGA         277
Leu Leu Ser Ala Glu Val Val Lys Ser Phe Leu Glu Lys Tyr Thr Gly
        15                  20                  25

TAT GGA ACT GTA TGT GCA TTG GAG GTT AAA CAG TCC AAA GGA GGA TCT         325
Tyr Gly Thr Val Cys Ala Leu Glu Val Lys Gln Ser Lys Gly Gly Ser
         30                  35                  40

AGA GCA TTT GCC AAA GTT CAA TTT GCC GAC AAC ATA AGT GCT GAC AAA         373
Arg Ala Phe Ala Lys Val Gln Phe Ala Asp Asn Ile Ser Ala Asp Lys
 45                  50                  55                  60

ATC ATC ACT TTG GCT AAT AAC AGG CTG TAT TTT GGC TCT TCT TAT TTG         421
Ile Ile Thr Leu Ala Asn Asn Arg Leu Tyr Phe Gly Ser Ser Tyr Leu
                 65                  70                  75

AAG GCT TGG GAA ATG AAA ACT GAT ATT GTC CAA CTG CGG GCA TAT GTG         469
Lys Ala Trp Glu Met Lys Thr Asp Ile Val Gln Leu Arg Ala Tyr Val
             80                  85                  90

GAT CAG ATG GAT GGC ATA ACT TTG AAT TTC GGA TGT CAG ATA TCA GAT         517
Asp Gln Met Asp Gly Ile Thr Leu Asn Phe Gly Cys Gln Ile Ser Asp
         95                 100                 105

GAC AAG TTT GCA GTG TTG GGA AGT ACA GAA GTT TCA ATT CAA TTT GGC         565
Asp Lys Phe Ala Val Leu Gly Ser Thr Glu Val Ser Ile Gln Phe Gly
    110                 115                 120

ATT GGA TTG AAG AAA TTT TTT TTC TTT TTA TCT AGT GGT TCA GCT GAC         613
Ile Gly Leu Lys Lys Phe Phe Phe Phe Leu Ser Ser Gly Ser Ala Asp
125                 130                 135                 140

TAT AAA CTT CAG CTT TCA TAT GAA AAT ATA TGG CAG GTT GTG CTC CAT         661
Tyr Lys Leu Gln Leu Ser Tyr Glu Asn Ile Trp Gln Val Val Leu His
                145                 150                 155

CGT CCA TAT GGT CAA AAT GCT CAG TTT CTC CTC ATA CAG TTA TTT GGT         709
Arg Pro Tyr Gly Gln Asn Ala Gln Phe Leu Leu Ile Gln Leu Phe Gly
            160                 165                 170
```

```
GCT CCT CGG ATC TAT AAG AGA CTT GAA AAC TCC TGT TAT AGC TTC TTT        757
Ala Pro Arg Ile Tyr Lys Arg Leu Glu Asn Ser Cys Tyr Ser Phe Phe
        175                 180                 185

AAG GAA ACT CCT GAT GAT CAG TGG GTG AGG ACA ACA GAT TTC CCT CCA        805
Lys Glu Thr Pro Asp Asp Gln Trp Val Arg Thr Thr Asp Phe Pro Pro
    190                 195                 200

TCT TGG ATA GGG CTA TCT TCT AGC TTA TGT TTG CAG TTC CGT AGG GGT        853
Ser Trp Ile Gly Leu Ser Ser Ser Leu Cys Leu Gln Phe Arg Arg Gly
205                 210                 215                 220

GTT CGT CTT CCA AAT TTC GAG GAA AGT TTT TTC CAC TAT GCA GAA CGT        901
Val Arg Leu Pro Asn Phe Glu Glu Ser Phe Phe His Tyr Ala Glu Arg
                225                 230                 235

GAA AAC AAT ATT ACT TTA CAG ACT GGT TTC ACC TTT TTC GTC TCT CAA        949
Glu Asn Asn Ile Thr Leu Gln Thr Gly Phe Thr Phe Phe Val Ser Gln
            240                 245                 250

AAA TCG GCT CTG GTT CCC AAT GTC CAG CCT CCG GAA GGA ATT TCA ATT        997
Lys Ser Ala Leu Val Pro Asn Val Gln Pro Pro Glu Gly Ile Ser Ile
        255                 260                 265

CCC TAC AAG ATT TTG TTC AAA ATT AGT TCT TTG GTA CAG CAT GGA TGC       1045
Pro Tyr Lys Ile Leu Phe Lys Ile Ser Ser Leu Val Gln His Gly Cys
    270                 275                 280

ATA CCT GGG CCA GCA TTA AAT GTC TAC TTT TTC CGA TTA GTT GAT CCT       1093
Ile Pro Gly Pro Ala Leu Asn Val Tyr Phe Phe Arg Leu Val Asp Pro
285                 290                 295                 300

CGA AGG AGA AAT GTG GCA TGC ATT GAG CAT GCC TTA GAG AAA CTG TAC       1141
Arg Arg Arg Asn Val Ala Cys Ile Glu His Ala Leu Glu Lys Leu Tyr
                305                 310                 315

TAT ATA AAG GAG TGC TGT TAT GAT CCC GTG AGG TGG CTC ACT GAG CAG       1189
Tyr Ile Lys Glu Cys Cys Tyr Asp Pro Val Arg Trp Leu Thr Glu Gln
            320                 325                 330

TAT GAT GGG TAT CTC AAG GGT AGA CAA CCT CCA AAA TCT CCG TCC ATC       1237
Tyr Asp Gly Tyr Leu Lys Gly Arg Gln Pro Pro Lys Ser Pro Ser Ile
        335                 340                 345

ACT TTA GAT GAT GGG TTG GTG TAT GTA AGA AGG GTC CTA GTA ACA CCA       1285
Thr Leu Asp Asp Gly Leu Val Tyr Val Arg Arg Val Leu Val Thr Pro
    350                 355                 360

TGC AAA GTT TAT TTT TGT GGT CCA GAG GTT AAT GTT TCC AAT CGG GTT       1333
Cys Lys Val Tyr Phe Cys Gly Pro Glu Val Asn Val Ser Asn Arg Val
365                 370                 375                 380

CTC CGC AAT TAT TCT GAA GAC ATA GAT AAC TTT CTT CGT GTT TCT TTT       1381
Leu Arg Asn Tyr Ser Glu Asp Ile Asp Asn Phe Leu Arg Val Ser Phe
                385                 390                 395

GTT GAT GAG GAG TGG GAG AAA CTG TAT TCT ACA GAC TTA TTA CCA AAA       1429
Val Asp Glu Glu Trp Glu Lys Leu Tyr Ser Thr Asp Leu Leu Pro Lys
            400                 405                 410

GCA AGT ACT GGA AGT GGT GTC AGG ACA AAC ATC TAT GAG AGG ATC TTA       1477
Ala Ser Thr Gly Ser Gly Val Arg Thr Asn Ile Tyr Glu Arg Ile Leu
        415                 420                 425

TCA ACT CTG CGG AAA GGC TTT GTA ATT GGT GAT AAA AAA TTT GAA TTT       1525
Ser Thr Leu Arg Lys Gly Phe Val Ile Gly Asp Lys Lys Phe Glu Phe
    430                 435                 440

CTT GCA TTT TCA TCG AGC CAG TTG CGG GAT AAT TCA GTG TGG ATG TTT       1573
Leu Ala Phe Ser Ser Ser Gln Leu Arg Asp Asn Ser Val Trp Met Phe
445                 450                 455                 460

GCA TCA AGA CCT GGC CTT ACT GCA AAT GAT ATA AGA GCT TGG ATG GGT       1621
Ala Ser Arg Pro Gly Leu Thr Ala Asn Asp Ile Arg Ala Trp Met Gly
                465                 470                 475

GAT TTT TCG CAG ATC AAG AAT GTC GCA AAA TAT GCT GCC AGA CTT GGT       1669
Asp Phe Ser Gln Ile Lys Asn Val Ala Lys Tyr Ala Ala Arg Leu Gly
            480                 485                 490
```

```
CAA TCT TTT GGT TCC TCC AGA GAG ACT TTG AGT GTT CTT AGG CAT GAG       1717
Gln Ser Phe Gly Ser Ser Arg Glu Thr Leu Ser Val Leu Arg His Glu
        495                 500                 505

ATT GAA GTT ATT CCC GAT GTA AAG GTT CAT GGA ACC AGC TAT GTC TTT       1765
Ile Glu Val Ile Pro Asp Val Lys Val His Gly Thr Ser Tyr Val Phe
510                 515                 520

TCT GAT GGA ATT GGT AAA ATA TCT GGT GAC TTT GCT CAT AGA GTT GCC       1813
Ser Asp Gly Ile Gly Lys Ile Ser Gly Asp Phe Ala His Arg Val Ala
525                 530                 535                 540

TCA AAA TGT GGC CTT CAA TAT ACC CCA TCT GCT TTC CAG ATT CGT TAT       1861
Ser Lys Cys Gly Leu Gln Tyr Thr Pro Ser Ala Phe Gln Ile Arg Tyr
            545                 550                 555

GGT GGA TAT AAA GGT GTT GTG GGT GTT GAT CCG GAT TCA TCA ATG AAG       1909
Gly Gly Tyr Lys Gly Val Val Gly Val Asp Pro Asp Ser Ser Met Lys
                560                 565                 570

TTG TCT TTG AGA AAG AGC ATG TCG AAA TAT GAA TCA GAC AAC ATA AAG       1957
Leu Ser Leu Arg Lys Ser Met Ser Lys Tyr Glu Ser Asp Asn Ile Lys
            575                 580                 585

TTA GAT GTC CTT GGA TGG AGC AAA TAT CAG CCT TGT TAT CTT AAT CGT       2005
Leu Asp Val Leu Gly Trp Ser Lys Tyr Gln Pro Cys Tyr Leu Asn Arg
590                 595                 600

CAA CTG ATT ACG CTC TTG TCT ACA CTT GGA GTG AAA GAT GAA GTT CTC       2053
Gln Leu Ile Thr Leu Leu Ser Thr Leu Gly Val Lys Asp Glu Val Leu
605                 610                 615                 620

GAA CAG AAG CAA AAG GAA GCT GTA GAT CAG CTT GAT GCT ATC TTG CAT       2101
Glu Gln Lys Gln Lys Glu Ala Val Asp Gln Leu Asp Ala Ile Leu His
            625                 630                 635

GAT TCT TTG AAG GCA CAG GAG GCT TTG GAA TTG ATG TCT CCT GGA GAG       2149
Asp Ser Leu Lys Ala Gln Glu Ala Leu Glu Leu Met Ser Pro Gly Glu
            640                 645                 650

AAC ACT AAT ATT CTC AAG GCA ATG CTA AAC TGT GGT TAT AAG CCT GAT       2197
Asn Thr Asn Ile Leu Lys Ala Met Leu Asn Cys Gly Tyr Lys Pro Asp
                655                 660                 665

GCT GAG CCC TTT CTT TCA ATG ATG TTG CAA ACC TTC CGC GCA TCC AAG       2245
Ala Glu Pro Phe Leu Ser Met Met Leu Gln Thr Phe Arg Ala Ser Lys
670                 675                 680

TTG CTC GAT TTG CGG ACT AGA TCA AGA ATA TTT ATT CCA AAT GGA AGA       2293
Leu Leu Asp Leu Arg Thr Arg Ser Arg Ile Phe Ile Pro Asn Gly Arg
685                 690                 695                 700

ACA ATG ATG GGA TGT TTG GAT GAA TCC AGA ACC TTG GAA TAT GGT CAG       2341
Thr Met Met Gly Cys Leu Asp Glu Ser Arg Thr Leu Glu Tyr Gly Gln
            705                 710                 715

GTG TTT GTT CAG TTT ACT GGT GCT GGA CAT GGA GAG TTT TCT GAC GAT       2389
Val Phe Val Gln Phe Thr Gly Ala Gly His Gly Glu Phe Ser Asp Asp
            720                 725                 730

TTA CAT CCA TTT AAT AAC AGC AGA TCC ACC AAC AGT AAT TTC ATT CTG       2437
Leu His Pro Phe Asn Asn Ser Arg Ser Thr Asn Ser Asn Phe Ile Leu
            735                 740                 745

AAG GGA AAT GTG GTT GTT GCA AAA AAT CCA TGC TTG CAT CCT GGT GAT       2485
Lys Gly Asn Val Val Val Ala Lys Asn Pro Cys Leu His Pro Gly Asp
750                 755                 760

ATT CGT GTT TTA AAG GCT GTA AAT GTT CGA GCG CTG CAC CAC ATG GTA       2533
Ile Arg Val Leu Lys Ala Val Asn Val Arg Ala Leu His His Met Val
765                 770                 775                 780

GAT TGT GTT GTA TTC CCT CAG AAA GGA AAA AGA CCT CAT CCG AAT GAA       2581
Asp Cys Val Val Phe Pro Gln Lys Gly Lys Arg Pro His Pro Asn Glu
                785                 790                 795

TGT TCT GGG AGT GAT TTG GAT GGG GAT ATC TAC TTT GTT TGC TGG GAT       2629
Cys Ser Gly Ser Asp Leu Asp Gly Asp Ile Tyr Phe Val Cys Trp Asp
                800                 805                 810
```

-continued

| | | |
|---|---|---|
| CAA GAC ATG ATC CCG CCA AGG CAA GTC CAG CCG ATG GAA TAT CCT CCA<br>Gln Asp Met Ile Pro Pro Arg Gln Val Gln Pro Met Glu Tyr Pro Pro<br>              815                  820                  825 | 2677 |

```
CAA GAC ATG ATC CCG CCA AGG CAA GTC CAG CCG ATG GAA TAT CCT CCA      2677
Gln Asp Met Ile Pro Pro Arg Gln Val Gln Pro Met Glu Tyr Pro Pro
            815                 820                 825

GCA CCC AGC ATA CAG TTG GAC CAT GAT GTC ACA ATT GAG GAA GTT GAA      2725
Ala Pro Ser Ile Gln Leu Asp His Asp Val Thr Ile Glu Glu Val Glu
830                 835                 840

GAG TAC TTC ACC AAC TAT ATT GTG AAT GAC AGT TTG GGA ATC ATA GCA      2773
Glu Tyr Phe Thr Asn Tyr Ile Val Asn Asp Ser Leu Gly Ile Ile Ala
845                 850                 855                 860

AAT GCC CAT GTC GTA TTT GCA GAC AGA GAA CCT GAT ATG GCC ATG AGT      2821
Asn Ala His Val Val Phe Ala Asp Arg Glu Pro Asp Met Ala Met Ser
            865                 870                 875

GAT CCA TGC AAA AAA CTT GCT GAG CTC TTT TCA ATT GCA GTG GAC TTT      2869
Asp Pro Cys Lys Lys Leu Ala Glu Leu Phe Ser Ile Ala Val Asp Phe
            880                 885                 890

CCA AAG ACT GGT GTT CCC GCT GAA ATA CCA TCT CAG TTG CGC CCT AAA      2917
Pro Lys Thr Gly Val Pro Ala Glu Ile Pro Ser Gln Leu Arg Pro Lys
            895                 900                 905

GAA TAC CCA GAC TTC ATG GAT AAG CCG GAC AAG ACC AGC TAT ATC TCA      2965
Glu Tyr Pro Asp Phe Met Asp Lys Pro Asp Lys Thr Ser Tyr Ile Ser
910                 915                 920

GAA AGA GTT ATT GGA AAG CTT TTC AGG AAA GTG AAG GAC AAA GCA CCT      3013
Glu Arg Val Ile Gly Lys Leu Phe Arg Lys Val Lys Asp Lys Ala Pro
925                 930                 935                 940

CAG GCT AGC TCT ATC GCG ACC TTC ACA AGA GAT GTT GCA AGG AGA TCA      3061
Gln Ala Ser Ser Ile Ala Thr Phe Thr Arg Asp Val Ala Arg Arg Ser
            945                 950                 955

TAT GAT GCT GAT ATG GAA GTT GAT GGA TTT GAA GAT TAC ATT GAC GAA      3109
Tyr Asp Ala Asp Met Glu Val Asp Gly Phe Glu Asp Tyr Ile Asp Glu
            960                 965                 970

GCT TTT GAC TAC AAA ACT GAA TAT GAC AAC AAG CTG GGT AAT TTA ATG      3157
Ala Phe Asp Tyr Lys Thr Glu Tyr Asp Asn Lys Leu Gly Asn Leu Met
            975                 980                 985

GAC TAC TAT GGC ATA AAA ACA GAG GCT GAA ATA CTT AGT GGT GGC ATT      3205
Asp Tyr Tyr Gly Ile Lys Thr Glu Ala Glu Ile Leu Ser Gly Gly Ile
990                 995                 1000

ATG AAG GCA TCA AAA ACT TTT GAC CGC AGA AAA GAT GCT GAG GCC ATT      3253
Met Lys Ala Ser Lys Thr Phe Asp Arg Arg Lys Asp Ala Glu Ala Ile
1005                1010                1015                1020

AGT GTT GCT GTG AGG GCC TTG AGG AAG GAG GCA AGA GCC TGG TTC AAG      3301
Ser Val Ala Val Arg Ala Leu Arg Lys Glu Ala Arg Ala Trp Phe Lys
                1025                1030                1035

AGG CGT AAT GAT ATA GAT GAC ATG TTA CCA AAG GCT TCG GCT TGG TAC      3349
Arg Arg Asn Asp Ile Asp Asp Met Leu Pro Lys Ala Ser Ala Trp Tyr
                1040                1045                1050

CAC GTT ACA TAT CAT CCT ACA TAT TGG GGT TGC TAC AAT CAG GGG TTG      3397
His Val Thr Tyr His Pro Thr Tyr Trp Gly Cys Tyr Asn Gln Gly Leu
                1055                1060                1065

AAA AGA GCT CAT TTC ATT AGC TTT CCC TGG TGT GTT TAT GAC CAG CTA      3445
Lys Arg Ala His Phe Ile Ser Phe Pro Trp Cys Val Tyr Asp Gln Leu
1070                1075                1080

ATC CAG ATT AAG AAG GAC AAA GCA CGT AAC AGG CCA GTT CTC AAC TTG      3493
Ile Gln Ile Lys Lys Asp Lys Ala Arg Asn Arg Pro Val Leu Asn Leu
1085                1090                1095                1100

TCA TCT CTC AGG GCT CAA CTG AGT CAC AGA TTA GTG TTG AAA              3535
Ser Ser Leu Arg Ala Gln Leu Ser His Arg Leu Val Leu Lys
                1105                1110

TGAGATTCCA GTCGAGCGTT AAGCTGATAT ATATATAATG TAATAGGGTG TGATCATAAG    3595

AAAACTGTTA TGCATTGTTG ACTACCTTTT GTCTTTAAAA CTGCATGAAG CTGCAACATA    3655
```

```
TATGCAGTAC TCTAAGAAAC AGATGTACAG CTAAGTACTA ATATGTATGT GATTTGAGTT    3715

TCATCTTTCT TCTAAA                                                   3731
```

(2) INFORMATION FOR SEQ ID NO: 2:

(i) SEQUENCE CHARACTERISTICS:
        (A) LENGTH: 1114 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Gly Lys Thr Ile Gln Val Phe Gly Phe Pro Tyr Leu Leu Ser Ala
  1               5                  10                  15

Glu Val Val Lys Ser Phe Leu Glu Lys Tyr Thr Gly Tyr Gly Thr Val
             20                  25                  30

Cys Ala Leu Glu Val Lys Gln Ser Lys Gly Gly Ser Arg Ala Phe Ala
         35                  40                  45

Lys Val Gln Phe Ala Asp Asn Ile Ser Ala Asp Lys Ile Ile Thr Leu
 50                  55                  60

Ala Asn Asn Arg Leu Tyr Phe Gly Ser Ser Tyr Leu Lys Ala Trp Glu
 65                  70                  75                  80

Met Lys Thr Asp Ile Val Gln Leu Arg Ala Tyr Val Asp Gln Met Asp
             85                  90                  95

Gly Ile Thr Leu Asn Phe Gly Cys Gln Ile Ser Asp Asp Lys Phe Ala
            100                 105                 110

Val Leu Gly Ser Thr Glu Val Ser Ile Gln Phe Gly Ile Gly Leu Lys
        115                 120                 125

Lys Phe Phe Phe Leu Ser Ser Gly Ser Ala Asp Tyr Lys Leu Gln
130                 135                 140

Leu Ser Tyr Glu Asn Ile Trp Gln Val Val Leu His Arg Pro Tyr Gly
145                 150                 155                 160

Gln Asn Ala Gln Phe Leu Leu Ile Gln Leu Phe Gly Ala Pro Arg Ile
                165                 170                 175

Tyr Lys Arg Leu Glu Asn Ser Cys Tyr Ser Phe Phe Lys Glu Thr Pro
            180                 185                 190

Asp Asp Gln Trp Val Arg Thr Thr Asp Phe Pro Pro Ser Trp Ile Gly
        195                 200                 205

Leu Ser Ser Ser Leu Cys Leu Gln Phe Arg Arg Gly Val Arg Leu Pro
210                 215                 220

Asn Phe Glu Glu Ser Phe Phe His Tyr Ala Glu Arg Glu Asn Asn Ile
225                 230                 235                 240

Thr Leu Gln Thr Gly Phe Thr Phe Phe Val Ser Gln Lys Ser Ala Leu
                245                 250                 255

Val Pro Asn Val Gln Pro Pro Glu Gly Ile Ser Ile Pro Tyr Lys Ile
            260                 265                 270

Leu Phe Lys Ile Ser Ser Leu Val Gln His Gly Cys Ile Pro Gly Pro
        275                 280                 285

Ala Leu Asn Val Tyr Phe Phe Arg Leu Val Asp Pro Arg Arg Arg Asn
290                 295                 300

Val Ala Cys Ile Glu His Ala Leu Glu Lys Leu Tyr Tyr Ile Lys Glu
305                 310                 315                 320

Cys Cys Tyr Asp Pro Val Arg Trp Leu Thr Glu Gln Tyr Asp Gly Tyr
                325                 330                 335
```

-continued

```
Leu Lys Gly Arg Gln Pro Pro Lys Ser Pro Ser Ile Thr Leu Asp Asp
            340                 345                 350
Gly Leu Val Tyr Val Arg Arg Val Leu Val Thr Pro Cys Lys Val Tyr
                355                 360                 365
Phe Cys Gly Pro Glu Val Asn Val Ser Asn Arg Val Leu Arg Asn Tyr
        370                 375                 380
Ser Glu Asp Ile Asp Asn Phe Leu Arg Val Ser Phe Val Asp Glu Glu
385                 390                 395                 400
Trp Glu Lys Leu Tyr Ser Thr Asp Leu Leu Pro Lys Ala Ser Thr Gly
                405                 410                 415
Ser Gly Val Arg Thr Asn Ile Tyr Glu Arg Ile Leu Ser Thr Leu Arg
                420                 425                 430
Lys Gly Phe Val Ile Gly Asp Lys Lys Phe Glu Phe Leu Ala Phe Ser
            435                 440                 445
Ser Ser Gln Leu Arg Asp Asn Ser Val Trp Met Phe Ala Ser Arg Pro
450                 455                 460
Gly Leu Thr Ala Asn Asp Ile Arg Ala Trp Met Gly Asp Phe Ser Gln
465                 470                 475                 480
Ile Lys Asn Val Ala Lys Tyr Ala Ala Arg Leu Gly Gln Ser Phe Gly
                485                 490                 495
Ser Ser Arg Glu Thr Leu Ser Val Leu Arg His Glu Ile Glu Val Ile
            500                 505                 510
Pro Asp Val Lys Val His Gly Thr Ser Tyr Val Phe Ser Asp Gly Ile
        515                 520                 525
Gly Lys Ile Ser Gly Asp Phe Ala His Arg Val Ala Ser Lys Cys Gly
        530                 535                 540
Leu Gln Tyr Thr Pro Ser Ala Phe Gln Ile Arg Tyr Gly Gly Tyr Lys
545                 550                 555                 560
Gly Val Val Gly Val Asp Pro Asp Ser Ser Met Lys Leu Ser Leu Arg
                565                 570                 575
Lys Ser Met Ser Lys Tyr Glu Ser Asp Asn Ile Lys Leu Asp Val Leu
                580                 585                 590
Gly Trp Ser Lys Tyr Gln Pro Cys Tyr Leu Asn Arg Gln Leu Ile Thr
            595                 600                 605
Leu Leu Ser Thr Leu Gly Val Lys Asp Glu Val Leu Glu Gln Lys Gln
        610                 615                 620
Lys Glu Ala Val Asp Gln Leu Asp Ala Ile Leu His Asp Ser Leu Lys
625                 630                 635                 640
Ala Gln Glu Ala Leu Glu Leu Met Ser Pro Gly Glu Asn Thr Asn Ile
                645                 650                 655
Leu Lys Ala Met Leu Asn Cys Gly Tyr Lys Pro Asp Ala Glu Pro Phe
            660                 665                 670
Leu Ser Met Met Leu Gln Thr Phe Arg Ala Ser Lys Leu Leu Asp Leu
        675                 680                 685
Arg Thr Arg Ser Arg Ile Phe Ile Pro Asn Gly Arg Thr Met Met Gly
        690                 695                 700
Cys Leu Asp Glu Ser Arg Thr Leu Glu Tyr Gly Gln Val Phe Val Gln
705                 710                 715                 720
Phe Thr Gly Ala Gly His Gly Glu Phe Ser Asp Asp Leu His Pro Phe
                725                 730                 735
Asn Asn Ser Arg Ser Thr Asn Ser Asn Phe Ile Leu Lys Gly Asn Val
            740                 745                 750
```

```
Val Val Ala Lys Asn Pro Cys Leu His Pro Gly Asp Ile Arg Val Leu
            755                 760                 765

Lys Ala Val Asn Val Arg Ala Leu His His Met Val Asp Cys Val Val
        770                 775                 780

Phe Pro Gln Lys Gly Lys Arg Pro His Pro Asn Glu Cys Ser Gly Ser
785                 790                 795                 800

Asp Leu Asp Gly Asp Ile Tyr Phe Val Cys Trp Asp Gln Asp Met Ile
                805                 810                 815

Pro Pro Arg Gln Val Gln Pro Met Glu Tyr Pro Pro Ala Pro Ser Ile
            820                 825                 830

Gln Leu Asp His Asp Val Thr Ile Glu Glu Val Glu Glu Tyr Phe Thr
        835                 840                 845

Asn Tyr Ile Val Asn Asp Ser Leu Gly Ile Ile Ala Asn Ala His Val
850                 855                 860

Val Phe Ala Asp Arg Glu Pro Asp Met Ala Met Ser Asp Pro Cys Lys
865                 870                 875                 880

Lys Leu Ala Glu Leu Phe Ser Ile Ala Val Asp Phe Pro Lys Thr Gly
                885                 890                 895

Val Pro Ala Glu Ile Pro Ser Gln Leu Arg Pro Lys Glu Tyr Pro Asp
            900                 905                 910

Phe Met Asp Lys Pro Asp Lys Thr Ser Tyr Ile Ser Glu Arg Val Ile
        915                 920                 925

Gly Lys Leu Phe Arg Lys Val Lys Asp Lys Ala Pro Gln Ala Ser Ser
    930                 935                 940

Ile Ala Thr Phe Thr Arg Asp Val Ala Arg Arg Ser Tyr Asp Ala Asp
945                 950                 955                 960

Met Glu Val Asp Gly Phe Glu Asp Tyr Ile Asp Glu Ala Phe Asp Tyr
                965                 970                 975

Lys Thr Glu Tyr Asp Asn Lys Leu Gly Asn Leu Met Asp Tyr Tyr Gly
            980                 985                 990

Ile Lys Thr Glu Ala Glu Ile Leu Ser Gly Gly Ile Met Lys Ala Ser
        995                 1000                1005

Lys Thr Phe Asp Arg Arg Lys Asp Ala Glu Ala Ile Ser Val Ala Val
    1010                1015                1020

Arg Ala Leu Arg Lys Glu Ala Arg Ala Trp Phe Lys Arg Arg Asn Asp
1025                1030                1035                1040

Ile Asp Asp Met Leu Pro Lys Ala Ser Ala Trp Tyr His Val Thr Tyr
                1045                1050                1055

His Pro Thr Tyr Trp Gly Cys Tyr Asn Gln Gly Leu Lys Arg Ala His
            1060                1065                1070

Phe Ile Ser Phe Pro Trp Cys Val Tyr Asp Gln Leu Ile Gln Ile Lys
        1075                1080                1085

Lys Asp Lys Ala Arg Asn Arg Pro Val Leu Asn Leu Ser Ser Leu Arg
    1090                1095                1100

Ala Gln Leu Ser His Arg Leu Val Leu Lys
1105                1110

(2) INFORMATION FOR SEQ ID NO: 3:

(i) SEQUENCE CHARACTERISTICS:
        (A) LENGTH: 218 amino acids
        (B) TYPE: amino acid
        (C) STRANDEDNESS: <Unknown>
        (D) TOPOLOGY: linear (ii) MOLECULE TYPE: protein
```

(xi) SEQUENCE DESCRIPTION: SEQ ID NO: 3:

```
Arg Thr Met Met Gly Cys Leu Asp Glu Ser Arg Thr Leu Glu Tyr Gl
1               5                   10                  15

Gln Val Phe Val Gln Phe Thr Gly Ala Gly His Gly Glu Phe Ser As
                20                  25                  30

Asp Leu His Pro Phe Asn Asn Ser Arg Ser Thr Asn Ser Asn Phe Il
                35                  40                  45

Leu Lys Gly Asn Val Val Val Ala Lys Asn Pro Cys Leu His Pro Gl
50                  55                  60

Asp Ile Arg Val Leu Lys Ala Val Asn Val Arg Ala Leu His His Me
65                  70                  75                  80

Val Asp Cys Val Val Phe Pro Gln Lys Gly Lys Arg Pro His Pro As
                85                  90                  95

Glu Cys Ser Gly Ser Asp Leu Asp Gly Asp Ile Tyr Phe Val Cys Tr
                100                 105                 110

Asp Gln Asp Met Ile Pro Pro Arg Gln Val Gln Pro Met Glu Tyr Pr
                115                 120                 125

Pro Ala Pro Ser Ile Gln Leu Asp His Asp Val Thr Ile Glu Glu Va
                130                 135                 140

Glu Glu Tyr Phe Thr Asn Tyr Ile Val Asn Asp Ser Leu Gly Ile Il
145                 150                 155                 160

Ala Asn Ala His Val Val Phe Ala Asp Arg Glu Pro Asp Met Ala Me
                165                 170                 175

Ser Asp Pro Cys Lys Lys Leu Ala Glu Leu Phe Ser Ile Ala Val As
                180                 185                 190

Phe Pro Lys Thr Gly Val Pro Ala Glu Ile Pro Ser Gln Leu Arg Pr
                195                 200                 205

Lys Glu Tyr Pro Asp Phe Met Asp Lys Pro
210                 215
```

(2) INFORMATION FOR SEQ ID NO: 4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 4:

CATAACGAAT CTGGAAAGCA GATGG                      25

(2) INFORMATION FOR SEQ ID NO: 5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 5:

GATGAATCCG GATCAACACC CACAC                      25

(2) INFORMATION FOR SEQ ID NO: 6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 6:

```
GGGTGCTGGA GGATATTCCA TCGGC                                      25
```

(2) INFORMATION FOR SEQ ID NO: 7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 7:

```
CTTCACCAGG GATCCACTCA TCACTCCCCT CAAG                            34
```

(2) INFORMATION FOR SEQ ID NO: 8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 8:

```
GCATAACTTC AGGGGGGATC CAGTTGGTGT TAGC                            34
```

(2) INFORMATION FOR SEQ ID NO: 9:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 9:

```
GCAGCTTCAT GCAGATCTAA AGACAAAAGG TAGTC                           35
```

(2) INFORMATION FOR SEQ ID NO: 10:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 10:

```
Ser Asn Arg Val Leu Arg Asn Tyr Ser Glu Asp Ile Asp Asn
1               5                   10
```

-continued

```
(2) INFORMATION FOR SEQ ID NO: 11:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 11:

Ala Ser Lys Thr Phe Asp Arg Arg Lys Asp Ala Glu Ala Ile
1               5                   10

(2) INFORMATION FOR SEQ ID NO: 12:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 12:

Glu Gln Tyr Asp Gly Tyr Leu Lys Gly Arg Gln Pro Pro Lys Ser Pr
1               5                   10                  15

Ser (2) INFORMATION FOR SEQ ID NO: 13:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 13:

Val Phe Pro Gln Lys Gly Lys Arg Pro His Asn Glu Cys
1               5                   10
```